(12) United States Patent
Rondoni et al.

(10) Patent No.: US 12,357,823 B2
(45) Date of Patent: Jul. 15, 2025

(54) SYSTEMS AND METHODS FOR TREATING INCONTINENCE

(71) Applicant: INSPIRE MEDICAL SYSTEMS, INC., Golden Valley, MN (US)

(72) Inventors: John Rondoni, Plymouth, MN (US); Stephen Lorne Bolea, Golden Valley, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 478 days.

(21) Appl. No.: 17/613,869

(22) PCT Filed: May 26, 2020

(86) PCT No.: PCT/US2020/034573
§ 371 (c)(1),
(2) Date: Nov. 23, 2021

(87) PCT Pub. No.: WO2020/243104
PCT Pub. Date: Dec. 3, 2020

(65) Prior Publication Data
US 2022/0288388 A1 Sep. 15, 2022

Related U.S. Application Data

(60) Provisional application No. 62/852,781, filed on May 24, 2019.

(51) Int. Cl.
*A61N 1/36* (2006.01)
(52) U.S. Cl.
CPC ................ *A61N 1/36007* (2013.01)

(58) Field of Classification Search
CPC .......................... A61N 1/36007; A61N 1/3606
See application file for complete search history.

(56) References Cited

U.S. PATENT DOCUMENTS

| | | | |
|---|---|---|---|
| 4,771,779 | A | 9/1988 | Tanagho et al. |
| 6,061,596 | A | 5/2000 | Richmond et al. |
| 6,354,991 | B1 | 3/2002 | Gross et al. |
| 6,652,449 | B1 | 11/2003 | Gross et al. |
| 6,712,772 | B2 | 3/2004 | Cohen et al. |
| 6,862,480 | B2 | 3/2005 | Cohen et al. |
| 6,907,293 | B2 | 6/2005 | Grill et al. |

(Continued)

FOREIGN PATENT DOCUMENTS

| | | |
|---|---|---|
| WO | 2003094693 A2 | 11/2003 |
| WO | 2007145913 A1 | 12/2007 |
| WO | 2011003072 A2 | 1/2011 |

OTHER PUBLICATIONS

Meyer et al., "Stimulated pressure profile at rest: a noninvasive method for assessing urethral sphincter function", Urology, vol. 52 (4), Oct. 1998, pp. 679-684.

(Continued)

*Primary Examiner* — Mark W. Bockelman
(74) *Attorney, Agent, or Firm* — DICKE, BILLIG & CZAJA, PLLC

(57) ABSTRACT

A system and/or method to treat incontinence of a patient includes a stimulation element implanted to stimulate one or more target sites to activate an external sphincter or other mechanism of continence of the patient, such as the external urethral sphincter and/or the external anal sphincter.

22 Claims, 21 Drawing Sheets

(56) References Cited

U.S. PATENT DOCUMENTS

| | | |
|---|---|---|
| 6,941,171 B2 | 9/2005 | Mann et al. |
| 7,047,078 B2 | 5/2006 | Boggs, II et al. |
| 7,054,689 B1 | 5/2006 | Whitehurst et al. |
| 7,239,918 B2 | 7/2007 | Strother et al. |
| 7,283,867 B2 | 10/2007 | Strother et al. |
| 7,328,068 B2 | 2/2008 | Spinelli et al. |
| 7,328,069 B2 | 2/2008 | Gerber |
| 7,343,202 B2 | 3/2008 | Mrva et al. |
| 7,369,894 B2 | 5/2008 | Gerber |
| 7,415,308 B2 | 8/2008 | Gerber et al. |
| 7,422,557 B2 | 9/2008 | Arnal et al. |
| 7,522,061 B2 | 4/2009 | Rondoni et al. |
| 7,571,000 B2 | 8/2009 | Boggs, II et al. |
| 7,580,752 B2 | 8/2009 | Gerber et al. |
| 7,590,453 B2 | 9/2009 | Heruth et al. |
| 7,610,093 B2 | 10/2009 | Gerber et al. |
| 7,613,516 B2 | 11/2009 | Cohen et al. |
| 7,623,925 B2 | 11/2009 | Grill et al. |
| 7,628,750 B2 | 12/2009 | Cohen et al. |
| 7,647,113 B2 | 1/2010 | Wirbisky et al. |
| 7,720,548 B2 | 5/2010 | King |
| 7,763,034 B2 | 7/2010 | Siegel et al. |
| 7,769,460 B2 | 8/2010 | Gerber |
| 7,855,653 B2 | 12/2010 | Rondoni et al. |
| 7,885,709 B2 | 2/2011 | Ben-David |
| 7,930,034 B2 | 4/2011 | Gerber |
| 8,108,049 B2 | 1/2012 | King |
| 8,121,691 B2 | 2/2012 | Gerber et al. |
| 8,121,702 B2 | 2/2012 | King |
| 8,145,323 B2 | 3/2012 | Gerber et al. |
| 8,160,710 B2 | 4/2012 | Buysman et al. |
| 8,190,253 B2 | 5/2012 | Heruth et al. |
| 8,190,262 B2 | 5/2012 | Gerber et al. |
| 8,195,296 B2 | 6/2012 | Longhini et al. |
| 8,204,597 B2 | 6/2012 | Gerber et al. |
| 8,295,933 B2 | 10/2012 | Gerber et al. |
| 8,380,312 B2 | 2/2013 | Gindele |
| 8,396,555 B2 | 3/2013 | Boggs, II et al. |
| 8,467,875 B2 | 6/2013 | Bennett et al. |
| 8,521,292 B2 | 8/2013 | Wei et al. |
| 8,649,870 B2 | 2/2014 | Mrva et al. |
| 8,706,232 B2 | 4/2014 | Su et al. |
| 8,706,233 B2 | 4/2014 | Su et al. |
| 8,744,585 B2 | 6/2014 | Gerber et al. |
| 8,761,888 B2 | 6/2014 | Gerber |
| 8,768,452 B2 | 7/2014 | Gerber |
| 8,805,508 B2 | 8/2014 | Gerber et al. |
| 8,825,163 B2 | 9/2014 | Grill et al. |
| 8,825,175 B2 | 9/2014 | King |
| 8,886,321 B2 | 11/2014 | Rohrer et al. |
| 8,989,861 B2 | 3/2015 | Su et al. |
| 9,026,226 B2 | 5/2015 | Gerber et al. |
| 9,061,146 B2 | 6/2015 | Gerber |
| 9,089,699 B2 | 7/2015 | Su et al. |
| 9,114,261 B2 | 8/2015 | Yonce |
| 9,155,885 B2 | 10/2015 | Wei et al. |
| 9,180,294 B2 | 11/2015 | Yonce |
| 9,185,489 B2 | 11/2015 | Gerber et al. |
| 9,192,763 B2 | 11/2015 | Gerber et al. |
| 9,192,764 B2 | 11/2015 | Rohrer et al. |
| 9,265,459 B2 | 2/2016 | Nagale et al. |
| 9,327,117 B2 | 5/2016 | Denison et al. |
| 9,393,411 B2 | 7/2016 | Bhadra et al. |
| 9,398,901 B2 | 7/2016 | Tischendorf et al. |
| 9,430,015 B2 | 8/2016 | Suzuki et al. |
| 9,433,783 B2 | 9/2016 | Wei et al. |
| 9,446,235 B2 | 9/2016 | Su et al. |
| 9,446,245 B2 | 9/2016 | Grill et al. |
| 9,539,433 B1 | 1/2017 | Wirbisky et al. |
| 9,724,511 B2 | 8/2017 | Wei et al. |
| 9,956,404 B2 | 5/2018 | Brink et al. |
| 10,035,020 B2 | 7/2018 | Wang et al. |
| 10,201,702 B2 | 2/2019 | Bonde et al. |
| 10,258,789 B2 | 4/2019 | Tischendorf et al. |
| 10,335,598 B2 | 7/2019 | Yonce |
| 10,441,785 B2 | 10/2019 | Harrah et al. |
| 10,456,580 B2 | 10/2019 | Brink et al. |
| 10,478,113 B2 | 11/2019 | Damaser et al. |
| 10,512,427 B2 | 12/2019 | Stone et al. |
| 10,518,086 B2 | 12/2019 | Su et al. |
| 11,045,649 B2 | 6/2021 | Wei et al. |
| 11,045,650 B2 | 6/2021 | Brink et al. |
| 11,116,980 B2 | 9/2021 | Nelson et al. |
| 11,202,908 B2 | 12/2021 | Su et al. |
| 11,213,340 B2 | 1/2022 | Su et al. |
| 11,419,533 B2 | 8/2022 | Damaser et al. |
| 2002/0055761 A1* | 5/2002 | Mann ................ A61N 1/36071 607/41 |
| 2004/0193228 A1 | 9/2004 | Gerber |
| 2005/0113878 A1 | 5/2005 | Gerber |
| 2006/0004421 A1 | 1/2006 | Bennett et al. |
| 2006/0020297 A1 | 1/2006 | Gerber et al. |
| 2007/0027495 A1* | 2/2007 | Gerber ............... A61N 1/36007 607/41 |
| 2007/0100388 A1 | 5/2007 | Gerber |
| 2007/0255176 A1 | 11/2007 | Rondoni et al. |
| 2007/0255333 A1 | 11/2007 | Giftakis et al. |
| 2008/0119898 A1 | 5/2008 | Ben-David et al. |
| 2008/0177398 A1 | 7/2008 | Gross et al. |
| 2009/0254144 A1 | 10/2009 | Bhadra et al. |
| 2010/0217340 A1 | 8/2010 | Watschke et al. |
| 2010/0274310 A1 | 10/2010 | Boggs, II et al. |
| 2011/0118805 A1* | 5/2011 | Wei .................... A61N 1/0551 607/41 |
| 2011/0301663 A1 | 12/2011 | Wang et al. |
| 2013/0041430 A1 | 2/2013 | Wang et al. |
| 2014/0309708 A1 | 10/2014 | Sharma |
| 2017/0043156 A1 | 2/2017 | Possover |
| 2018/0214691 A1 | 8/2018 | Famm et al. |
| 2019/0060647 A1 | 2/2019 | Su et al. |
| 2019/0126028 A1 | 5/2019 | Tischendorf et al. |
| 2019/0269924 A1 | 9/2019 | Su et al. |
| 2019/0269942 A1 | 9/2019 | Alford et al. |
| 2020/0376255 A1 | 12/2020 | Tischendorf et al. |
| 2020/0376256 A1 | 12/2020 | Tischendorf et al. |
| 2020/0398042 A1 | 12/2020 | Tischendorf et al. |
| 2021/0031032 A1 | 2/2021 | Zirpel et al. |
| 2021/0299442 A1 | 9/2021 | Wei et al. |
| 2021/0316145 A1 | 10/2021 | Offutt et al. |
| 2021/0361952 A1 | 11/2021 | Bonde et al. |
| 2021/0379373 A1 | 12/2021 | Hincapie et al. |
| 2022/0096845 A1 | 3/2022 | Deininger et al. |
| 2022/0096846 A1 | 3/2022 | Deininger et al. |
| 2022/0331584 A1 | 10/2022 | Offutt et al. |
| 2022/0331586 A1 | 10/2022 | Offutt et al. |
| 2022/0331589 A1 | 10/2022 | Bittner et al. |

OTHER PUBLICATIONS

Nissenkorn et al., "Patient-adjusted intermittent electrostimulation for treating stress and urge urinary incontinence", BJU International, vol. 94, Jul. 2004, pp. 105-109.

Gómez et al., "Treatment of stress urinary incontinence with perineal biofeedback by using superficial electrodes", Actas Urológicas Españolas, Abstract, 32(6):629-636, Jun. 1, 2008. DOI:10.1016/s0210-4806(08)73899-3, pp. 1-3.

Fall et al., "Long-term intravaginal electrical stimulation in urge and stress incontinence", Scandinavian Journal of Urology and Nephrology. Supplementum, Abstract, 44:55-63, Feb. 1977. PMID: 308693, pp. 1-3.

* cited by examiner

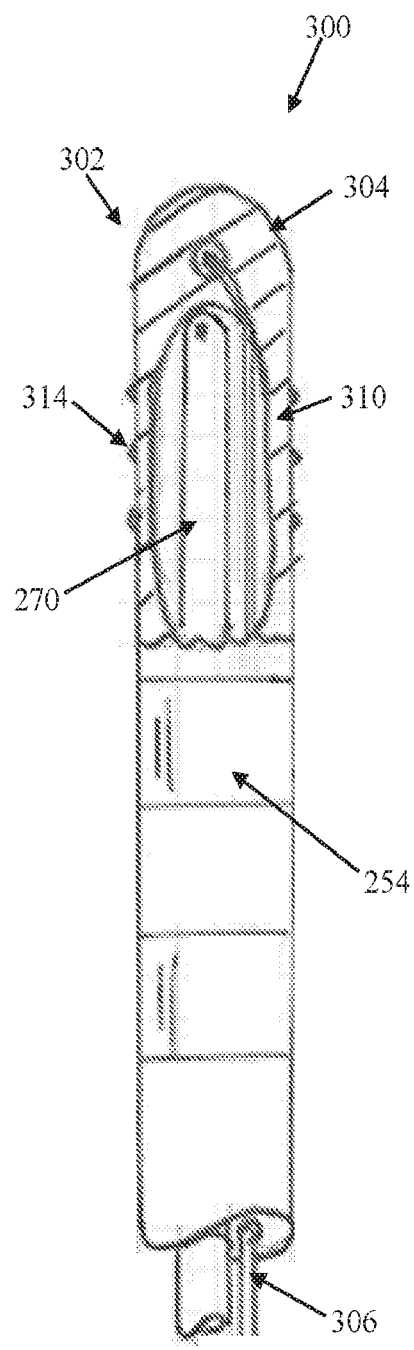
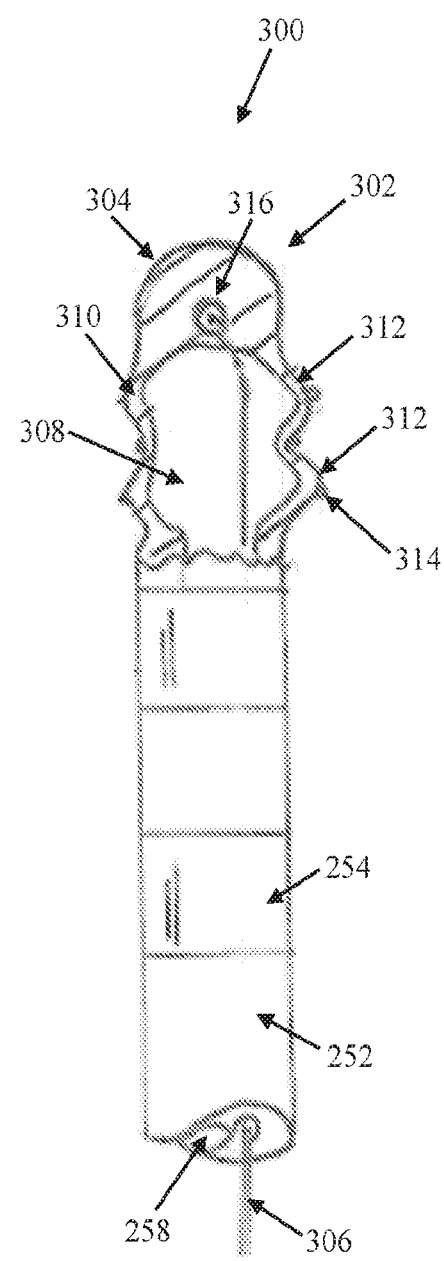
FIG. 10A
FIG. 10B

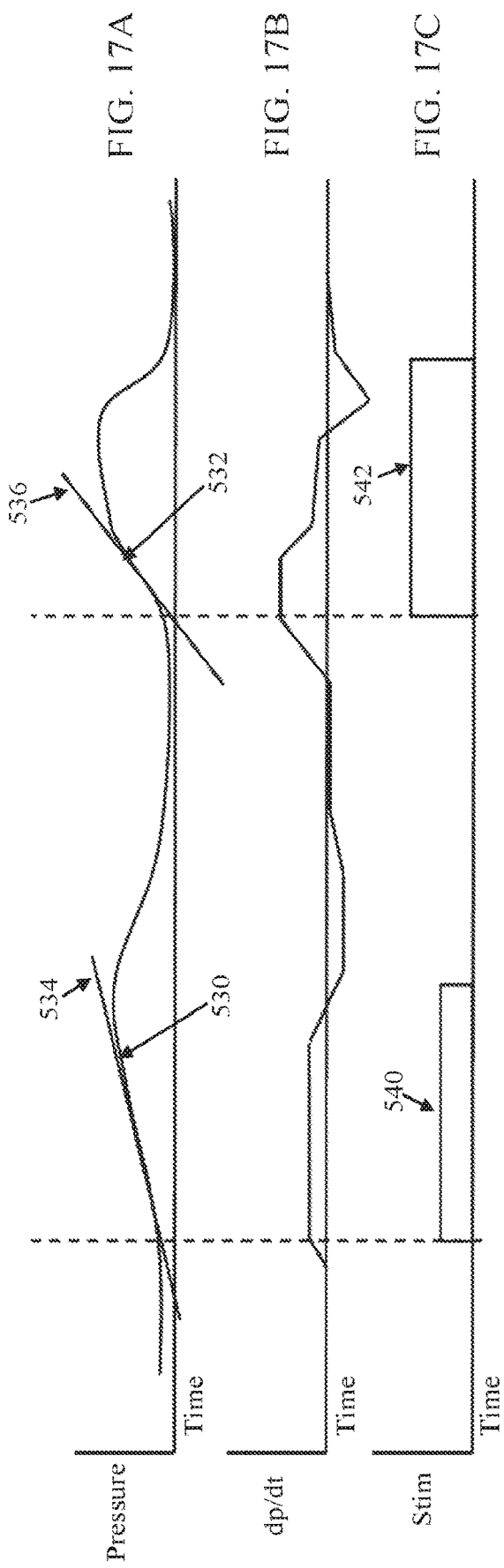

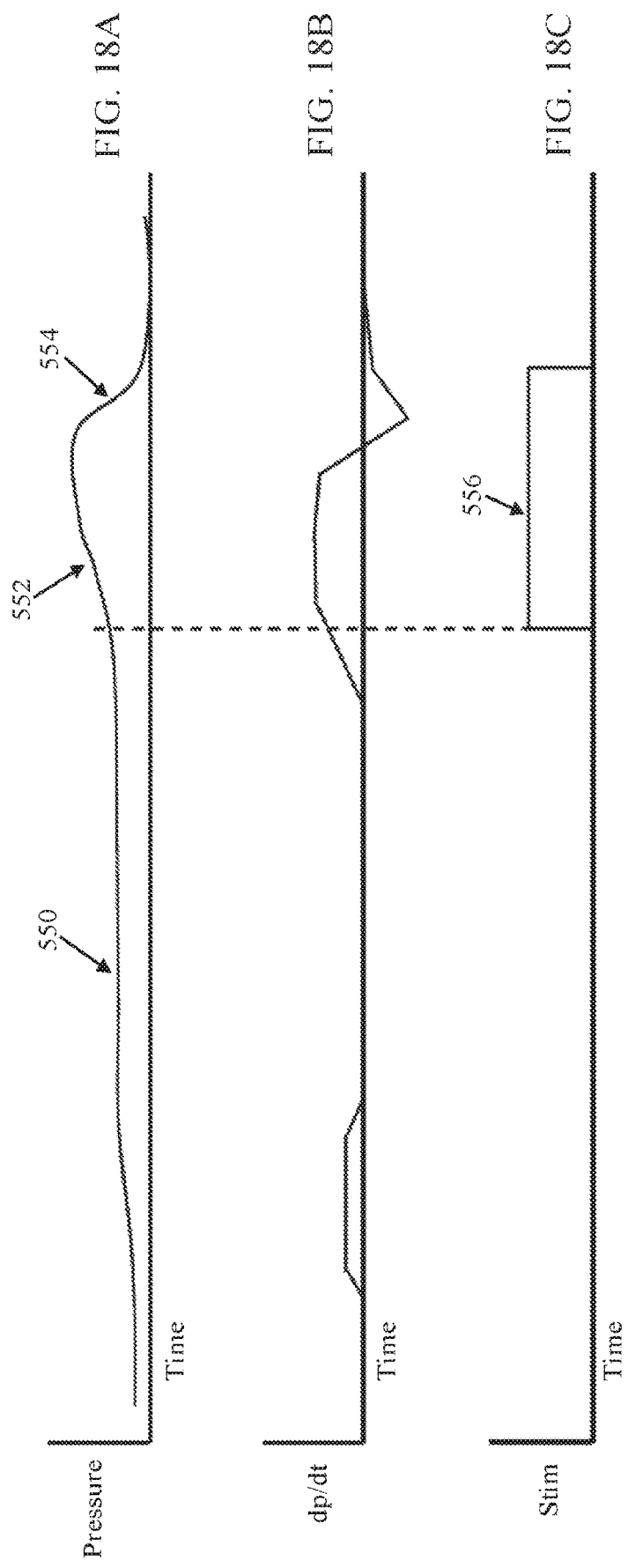

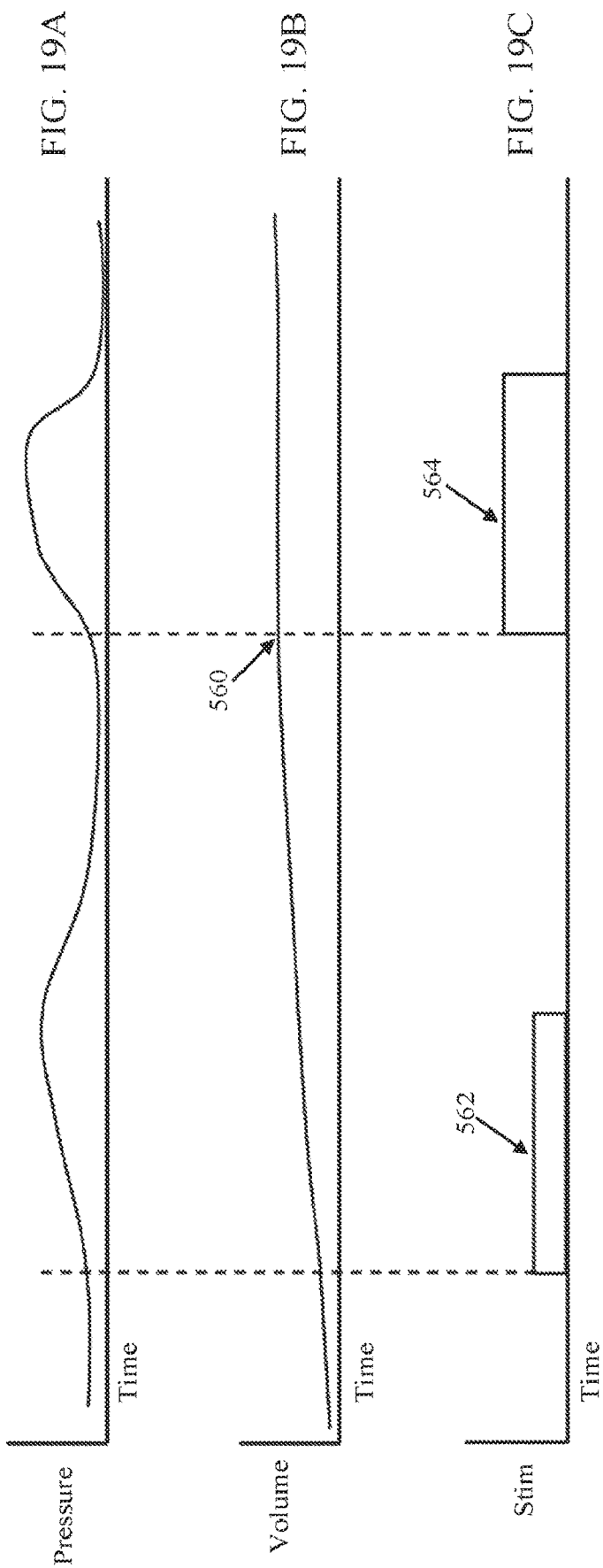

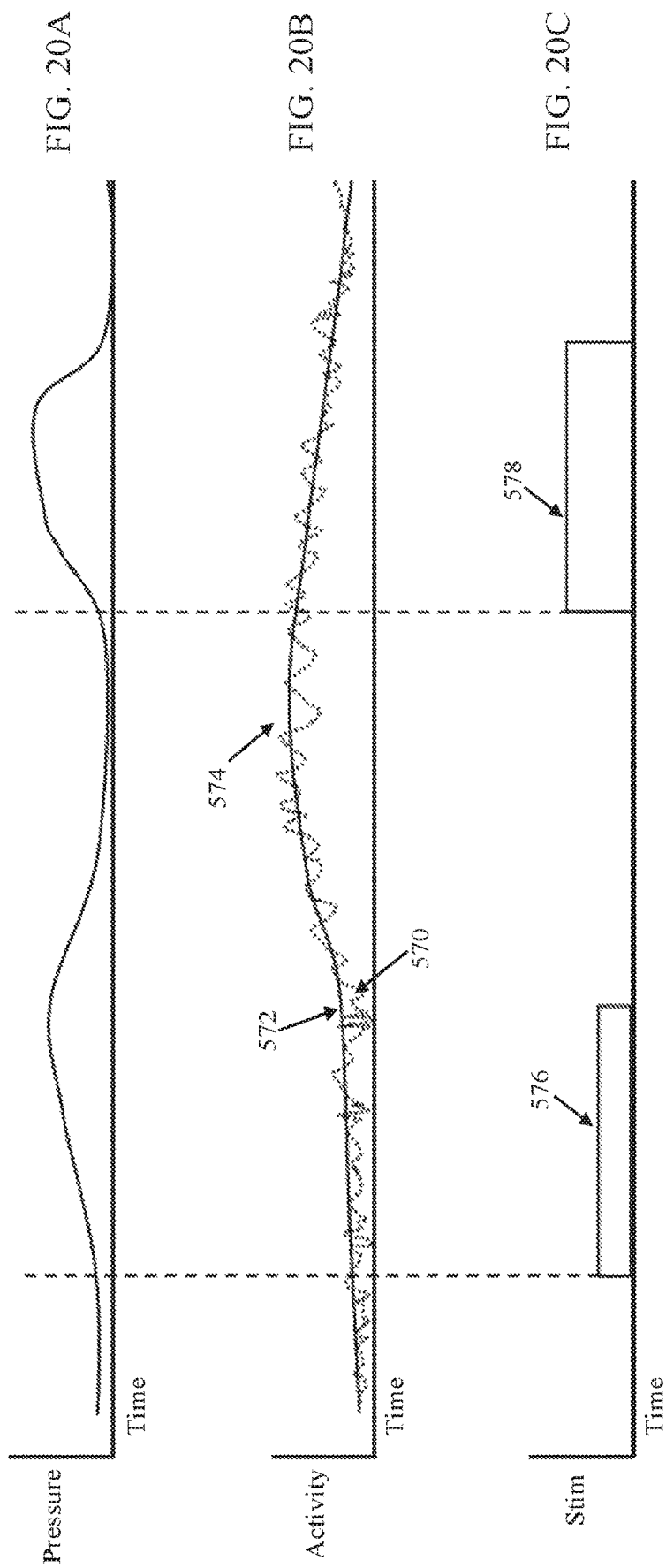

SYSTEMS AND METHODS FOR TREATING INCONTINENCE

CROSS-REFERENCE TO RELATED APPLICATIONS

This 35 U.S.C. § 371 National Phase application claims priority to International Application No. PCT/US2020/034573, filed May 26, 2020, which claims the benefit of U.S. Provisional Patent Application No. 62/852,781 filed May 24, 2019, the entire teachings of each of which are hereby incorporated by reference.

A portion of the population suffers from incontinence, such as one or both of urinary incontinence (or bladder incontinence) and fecal incontinence (or bowel incontinence). Diet, training, slings, and drug therapies may fail to treat incontinence.

BRIEF DESCRIPTION OF DRAWINGS

FIG. 10A is a simplified, side perspective view of a portion of lead assembly useful with the systems and methods of the present disclosure in a delivery state, along with a stylet.

FIG. 10B is a simplified, side perspective view of the lead assembly and stylet of FIG. 10A arranged in a deployed state.

FIGS. 17A-17C are graphs illustrating algorithms useful with systems and methods of the present disclosure for applying stimulation energy in the treatment of incontinence.

FIGS. 18A-18C are graphs illustrating algorithms useful with systems and methods of the present disclosure for applying stimulation energy in the treatment of incontinence.

FIGS. 19A-19C are graphs illustrating algorithms useful with systems and methods of the present disclosure for applying stimulation energy in the treatment of incontinence.

FIGS. 20A-20C are graphs illustrating algorithms useful with systems and methods of the present disclosure for applying stimulation energy in the treatment of incontinence.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to implantable devices for diagnosis, therapy, and/or other care of medical conditions. At least some examples may comprise implantable devices and/or methods of implanting devices useful for treating incontinence, including one or both of urinary incontinence and fecal incontinence of a patient, or other pelvic disorders. At least some such examples comprise implanting an electrode to deliver a nerve-stimulation signal to one or more nerves or nerve branches to activate a corresponding external sphincter, such as a branch of the pudendal nerve that activates the external urethral sphincter and/or the external anal sphincter. In some embodiments, operation of the implantable device is controlled in response to sensed information of the patient.

Figure 1:
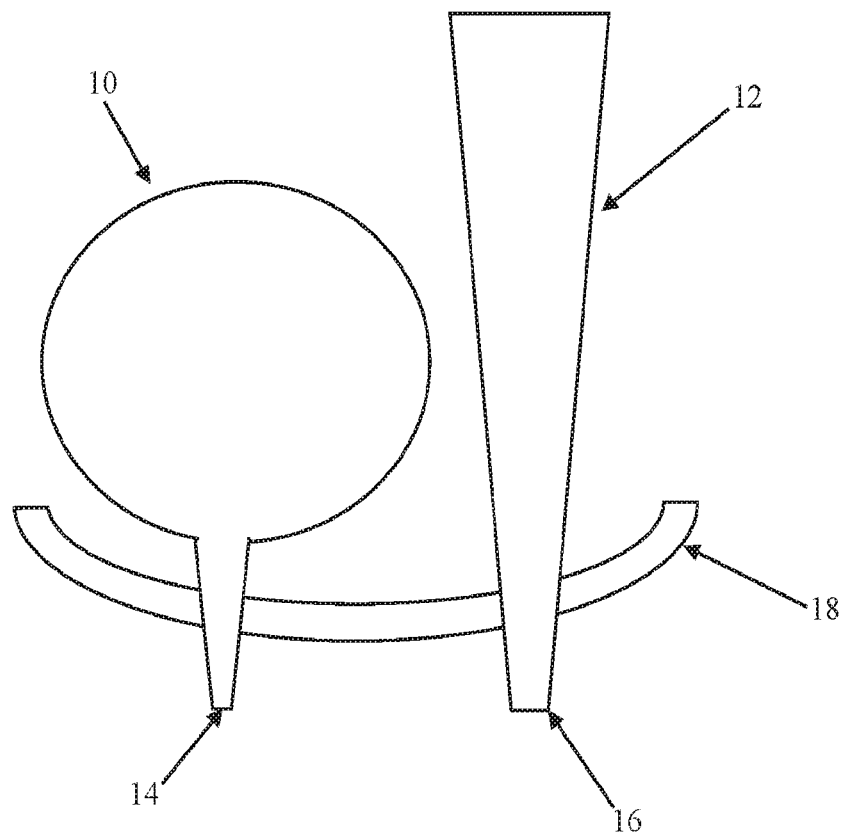
FIG. 1 is a schematic illustration of anatomy of a human pelvic region.

With reference to the greatly simplified view of FIG. 1, the human pelvic region includes a bladder 10 and a rectum 12. Contents of the bladder 10 are evacuated through a urethra 14, whereas contents of the rectum 12 are evacuated through anus 16. Pelvic floor muscles 18 support the pelvic organs and span the bottom of the pelvis. The pelvic floor muscle layer 18 has holes for passage of the urethra 14 and the anus 16, and normally wraps quite firmly around these holes to help keep the passages shut.

Figure 2:
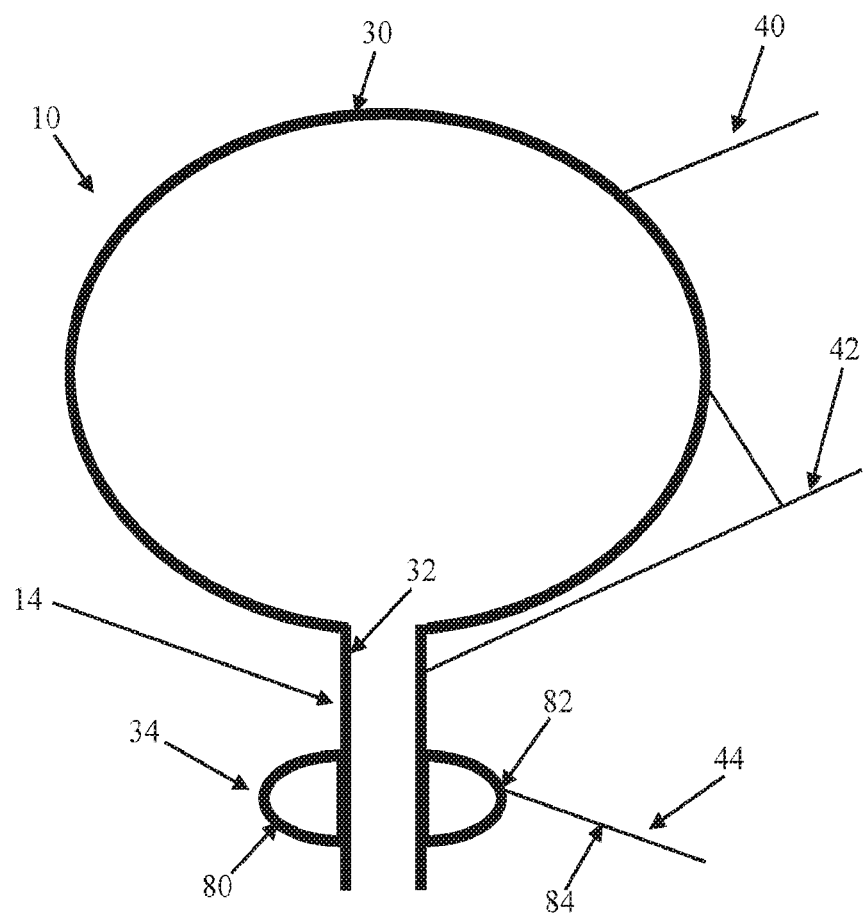
FIG. 2 is a schematic illustration of the pelvic region of FIG. 1 and various nerves.

With additional references to the greatly simplified view of FIG. 2, the bladder 10 is a hollow muscular organ connected to the kidneys by the ureters. The detrusor 30 muscle (referenced generally) is smooth muscle found in the wall of the bladder 10. The urethra 14 is a tube or duct by which urine is conveyed out of the body from the bladder 10. Internal and external sphincters control flow of urine through the urethra 14; under normal conditions, when either of these muscles contracts, the urethra 14 is sealed shut. In particular, an internal urethral sphincter (IUS) 32 (referenced generally) is a smooth muscle that constricts the internal orifice of the urethra 14. The IUS 32 is located at the junction of the urethra 14 with the bladder 10 and is continuous with the detrusor muscle 30, but is anatomically and functionally fully independent from the detrusor muscle 30. An external urethral sphincter (EUS) 34 is located in the deep perineal pouch, at the bladder's 10 distal inferior end in females and inferior to the prostate in males. Urine is excreted from the kidneys and stored in the bladder 10 before elimination via the urethra 14 during what is known as the micturition reflex. During periods of bladder filling, the storage of urine is promoted by the actions of the internal and external urethral sphincters 32, 34 and the pelvic floor musculature 18. During micturition, these sphincters 32, 34 relax and the smooth muscle of the bladder (the detrusor muscle 30) contracts, resulting in the expulsion of urine.

The body of the bladder 10 is directly innervated by efferent fibers that arise from parasympathetic postganglionic neurons in the pelvic ganglia and intramural ganglia and by efferent fibers that arise from sympathetic postganglionic neurons in the lumbosacral sympathetic chain and hypogastric ganglia/pelvic ganglia. This is generally reflected in FIG. 2 by reference to a pelvic nerve 40 and a hypogastric nerve 42. The internal urethral sphincter 32 receives innervation from the hypogastric nerve 42. The external urethral sphincter 34 is directly innervated by motor neurons in the sacral segments of the spinal cord via the pudendal nerve 44.

Urinary continence is generally defined as the act of storing urine in the bladder 10 until the bladder 10 can be appropriately evacuated. Urinary continence requires control of the detrusor muscle 30 and is the result of complex coordination between multiple centers in the brain, brain stem, spinal cord, and peripheral nerves. As described above, micturition is a coordinated act of bladder elimination that involves relaxing the pelvic floor muscles 18, contracting the detrusor muscle 30, and simultaneously opening the urethral sphincters 32, 34 to achieve complete emptying of the bladder. Stress incontinence can be defined as the involuntary leakage of urine from the bladder 10 accompanying physical activity (e.g., laughing, coughing, sneezing, etc.) which places increased pressure on the abdomen. The leakage occurs even though the bladder muscles (detrusor muscle 30) is not contracting and an urge to urinate is not present. Stress incontinence can develop when the urethral sphincters 32, 34, the pelvic floor muscles 18, or all of these structures have been weakened or damaged and cannot dependably hold in urine. With urethral hypermobility, the bladder 10 and urethra 14 shift downward when abdominal pressure rises, and there is no hammock-like support for the urethra 14 to be compressed against to keep it closed. With urethral incompetence, problems in the urinary sphincter 32, 34 keep it from closing fully or allow it to pop open under pressure. Urinary urge incontinence ("UUI") (sometimes referred to as overactive bladder ("OAB") or detrusor overactivity) entails the involuntary leakage of urine from the bladder 10 when a sudden strong need to urinate is felt. There is a sudden involuntary contraction of the muscular wall (the detrusor 30) of the bladder that signals an immediate need to urinate, which can happen even when the bladder 10 is not full. Mixed incontinence is the term used to a combination of both overactive bladder and stress incontinence.

Internal and external sphincters are similarly provided with the anus 16 (i.e., the internal anal sphincter and the external anal sphincter), acting to keep the anal canal and orifice closed. Action of the internal anal sphincter (IAS) is entirely involuntary, and it is in a state of continuous maximal contraction. The external anal sphincter (EAS) is always in a state of contraction, but can be voluntarily put into a condition of greater contraction so as to more firmly occlude the anal orifice. Similar to urinary continence, bowel continence is the act of storing feces until an acceptable time and opportunity for elimination. Bowel continence requires competent internal and external sphincters, pelvic floor musculature, and intact neurological pathways. Neurological control of bowel continence is complex and requires coordinated reflex activities from the autonomic and enteric nervous systems. The colon can be visualized as a closed, pliant tube bounded by the ileocecal valve and the anal sphincter. The continuous, smooth muscle layer at the end of the rectum 12 thickens to form the internal anal sphincter (IAS); the external anal sphincter (EAS) is a circular band of striated muscle that contracts with the pelvic floor. Parasympathetic stimulation of the IAS from the pelvic plexus originates from the sacral cord (S1 to S2). Sympathetic stimulation of the IAS causes contraction. The EAS is composed of both smooth and striated muscle. The smooth muscle of the EAS is innervated by the enteric nervous system. The striated component of the EAS is innervated by the pudendal nerve that exits the cord at sacral levels S2, S3, and S4.

Fecal incontinence can be defined as the involuntary loss of rectal contents (feces, gas) through the anal canal and the inability to postpone an evacuation until socially convenient. For example, injuries to one or both of the EAS and IAS may make it difficult to hold stool back properly. Injury to the nerves that sense stool in the rectum or those that control the anal sphincter can also lead to fecal incontinence. A generalized weakness of the pelvic floor 18 can lead to an impaired barrier to stool in the rectum 12 entering the anal canal, and this is associated with incontinence to solids. The pelvic floor 18 is innervated by the pudendal nerve and the S3 and S4 branches of the pelvic plexus. If the pelvic floor muscles 18 lose their innervation, they cease to contract and their muscle fibers are in time replaced by fibrous tissue, which is associated with pelvic floor weakness and incontinence.

With the above in mind, some example systems and/or methods of the present disclosure relate to treating one or more of urinary incontinence, UUI and fecal incontinence by supplying stimulation signals to an electrode implanted to apply the stimulation signal to one or more nerves and/or muscles of the patient as described in greater detail below.

In related systems and methods, monitoring, diagnosis and/or stimulation therapy can be implicated.

Figure 3:
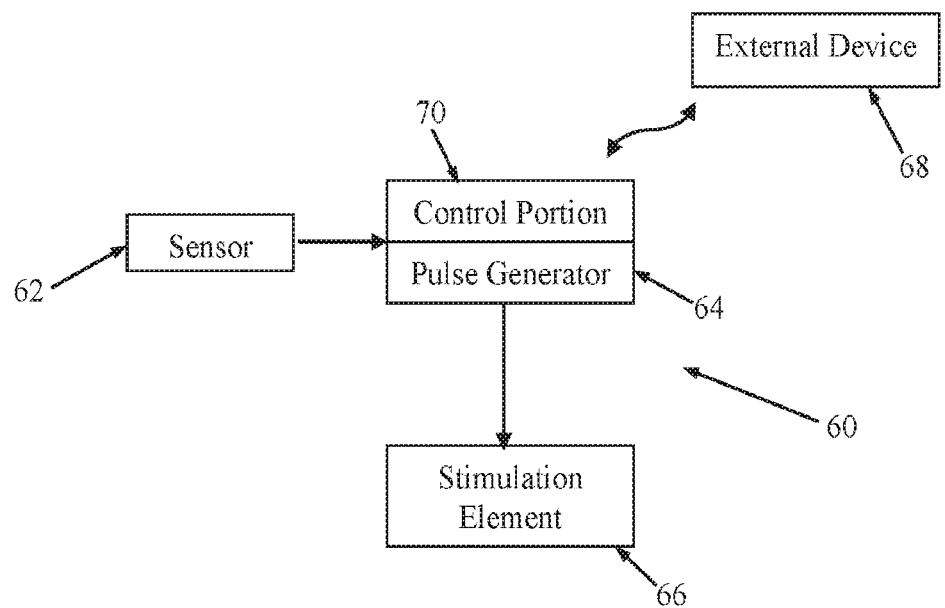
FIG. 3 is a block diagram of a treatment system in accordance with principles of the present disclosure.

One example of a treatment system 50 in accordance with principles of the present disclosure is provided in FIG. 3 and includes an implantable medical device (IMD) 60 (referenced generally) and one or more sensors 62. Details on the various components are provided below. In general terms, the IMD 60 includes an implantable pulse generator (IPG) 64 and one or more stimulation elements (e.g., electrode or electrode assembly) 66. The IPG 64 is configured for implantation into a patient, and is configured to provide and/or assist in the performance of therapy to the patient. The stimulation element 66 is configured to be implanted proximate a selected segment or region of the patient's anatomy, and is electrically connected to the IPG 64. The IPG 64 is programmed to deliver (or is prompted to deliver) stimulation signals to the stimulation element 66 that in turn apply the signal. In some embodiments, the IPG 64 is programmed (or is prompted) to initiate, cease and/or modulate (e.g., titrate) delivered stimulation signals based upon one or more physical parameters of the patient. In this regard, the sensor(s) 62 senses the physical parameter of interest, and signals the so-sensed parameter to the IPG 64 (or other component controlling operation of the IPG 64). The sensor 62 can be carried by the IPG 64, can be connected to the IPG 64, or can be a standalone component not physically connected to the IPG 64. In some embodiments, the treatment system 50 can further include an optional external device 68. Where provided, the external device 68 can, in some non-limiting embodiments, wirelessly communicate with the IMD 60.

The IPG 64 can assume various forms known in the art for generating a nerve-stimulating signal for delivery to the stimulation element(s) 66. For example, the IPG 64 can include a sealed case or enclosure maintaining a power source (e.g., battery) and electrical/circuitry components appropriate for formatting energy from the power source as the desired stimulation signal (e.g., a nerve-stimulation signal). In some embodiments, the IPG 64 as provided as part of, or is electronically linked to, a control system that includes a control portion 70 providing one example implementation of a control portion forming a part of, implementing, and/or generally managing stimulation element(s), power/control elements (e.g. pulse generators, microstimulators), sensors, and related elements, devices, user interfaces, instructions, information, engines, elements, functions, actions, and/or methods, as described throughout examples of the present disclosure. In some examples, the control portion 70 includes a controller and a memory. In general terms, the controller comprises at least one processor and associated memories. The controller is electrically couplable to, and in communication with, memory to generate control signals to direct operation of at least some of the stimulation elements, power/control elements (e.g. pulse generators, microstimulators) sensors, and related elements, devices, user interfaces, instructions, information, engines, elements, functions, actions, and/or methods, as described throughout examples of the present disclosure. In some non-limiting examples, these generated control signals include, but are not limited to, employing instructions and/or information stored in the memory to at least direct and manage treatment of incontinence by stimulating nerve(s), nerve branch(es) and/or muscle(s) to activate one or more of the external urethral sphincter 34 and the external anal sphincter, and/or pelvic floor nerves (e.g., the pudendal nerve 44, the sacral nerve) to relax the detrusor muscle 30 and prevent or reduce urgency or frequency. In some instances, the controller or control portion 70 may sometimes be referred to as being programmed to perform the actions, functions, routines, etc. of the present disclosure. In some examples, at least some of the stored instructions are implemented as, or may be referred to as, a care engine, a sensing engine, monitoring engine, and/or treatment engine. In some examples, at least some of the stored instructions and/or information may form at least part of, and/or, may be referred to as a care engine, sensing engine, monitoring engine, and/or treatment engine.

In response to or based upon commands received via a user interface and/or via machine readable instructions, the controller generates control signals as described above in accordance with at least some of the examples of the present disclosure. In some examples, the controller is embodied in a general purpose computing device while in some examples, the controller is incorporated into or associated with at least some of the stimulation elements, power/control elements (e.g. pulse generators, microstimulators), sensors, and related elements, devices, user interfaces, instructions, information, engines, functions, actions, and/or method, etc. as described throughout examples of the present disclosure.

For purposes of the present disclosure, in reference to the controller, the term "processor" shall mean a presently developed or future developed processor (or processing resources) that executes machine readable instructions contained in a memory. In some examples, execution of the machine readable instructions, such as those provided via the memory of the control portion 70 cause the processor to perform the above-identified actions, such as operating the controller to implement the sensing, monitoring, treatment, etc. as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by the memory. In some examples, the machine readable instructions may comprise a sequence of instructions, a processor-executable machine learning model, or the like. In some examples, the memory comprises a computer readable tangible medium providing non-volatile storage of the machine readable instructions executable by a process of the controller. In some examples, the computer readable tangible medium may sometimes be referred to as, and/or comprise at least a portion of, a computer program product. In other examples, hard wired circuitry may be used in place of or in combination with machine readable instructions to implement the functions described. For example, the controller may be embodied as part of at least one application-specific integrated circuit (ASIC), at least one field-programmable gate array (FPGA), and/or the like. In at least some examples, the controller is not limited to any specific combination of hardware circuitry and machine readable instructions, nor limited to any particular source for the machine readable instructions executed by the controller.

In some examples, the control portion 70 may be entirely implemented within or by a stand-alone device.

In some examples, the control portion 70 may be partially implemented in the IPG 64 and partially implemented in a computing resource separate from, and independent of, the IPG 64. For instance, in some examples the control portion 70 may be implemented via a server accessible via the cloud and/or other network pathways. In some examples, the control portion 70 may be distributed or apportioned among multiple devices or resources such as among a server, a congestive heart failure treatment device (or portion thereof), and/or a user interface.

In some examples, the control portion 70 is entirely implemented within or by the IPG 64 (thereby defining an IPG assembly), which has at least some of substantially the same features and attributes as a pulse generator (e.g. power/control element, microstimulator) as previously described throughout the present disclosure. In some examples, the control portion 70 is entirely implemented within or by a remote control (e.g. a programmer) external to the patient's body, such as a patient control and/or a physician control (e.g., the external device 68). In some examples, the control portion 70 is partially implemented in the IPG 64 assembly and partially implemented in the remote control (at least one of the patient control and the physician control).

Stimulation Target Sites

With reference between FIGS. 1-3, as described in greater detail below, the system 50 can be configured and implanted to provide stimulation therapy to one or more nerves and/or muscles that, for example, influence the behavior of musculature of the pelvic region of the patient, for example musculature relating to one or both of urinary incontinence and fecal incontinence (e.g., the external urethral sphincter 34, the internal urethral sphincter 32, pelvic floor muscles 18, the external anal sphincter, the internal anal sphincter, etc.). For example, stimulation can be provided to one or more of the pudendal nerve 44, the pelvic nerve 40, the sacral nerve, or branches thereof. Alternatively or in addition, the system 50 can apply electrical stimulation to tissue sites proximate a nerve or nerve branch of interest. In yet other embodiments, stimulation can be applied directly to a muscle.

In yet other embodiments, stimulation energy can be applied to one or more other nerves implicating bladder and/or anal control. As a point of reference, various nerves relevant to urinary continence and/or micturition include the pudendal nerve 44, pelvic nerve 40, and hypogastric nerve 42. The hypogastric nerve 42 is part of the sympathetic nervous system, and can inhibit contraction of the detrusor muscle as well as activate or contract the muscles of the urethra (and the neck of the bladder). With some embodiments of the present disclosure, stimulation energy is applied to the hypogastric nerve(s) 42 at the S, T or L level (e.g., sympathetic nerves T10-L2) in a manner that encourages the body's natural, unconscious or reflexive control over voiding, for example to prevent leakage. In other embodiments, stimulation energy is applied to the pelvic splanchnic nerves (or other parasympathetic nerve implicating urinary or fecal continence) at the S, T or L level (from T11, T12-L1, L2) in a manner that suppresses parasympathetic nerve impulses otherwise "activating" the patient's normal micturition drive; this, in turn, can enhance continence by allowing greater sympathetic nerve activity or through a relax action that has similar benefit.

In some non-limiting embodiments, the external urethral sphincter 34 is the structure targeted to be affected by the systems and methods of the present disclosure. In addition or alternatively, the internal urethral sphincter 32 can be targeted for contraction with the systems and methods of the present disclosure, for example by direct muscle stimulation, stimulation of the pelvic or hypogastric nerves, etc. In yet other embodiments, the systems and methods of the present disclosure can apply stimulation energy to affect one or more pelvic floor muscles 18 (or other structures of the pelvic floor) that implicate continence, such as the levator ani, the compressor urethrae, the urethrovaginal sphincter, the bulbospongiosus, the pubovaginalis, etc.

As is evident from the descriptions of the present disclosure, with some example systems and methods of the present disclosure, stimulation energy can be applied to one, two, three or more target sites, and information can be sensed from one, two, or more target sites. In some non-limiting embodiments, a first stimulation element is located to apply stimulation energy intended to activate the external urethral sphincter 34 and a second stimulation element is located to apply stimulation energy intended to activate the external anal sphincter (so as to treat both urinary and fecal incontinence). In other embodiments, the second stimulation element can be located to activate the pelvic floor muscles 18 (e.g., to elevate the bladder 10 of a patient suffering from bladder prolapse). The first and second stimulation elements can be driven by the same IPG 64, or two (or more) IPG's can be provided. With some systems and methods of the present disclosure, stimulation elements are located to stimulate at least two, optionally all, of the hypogastric nerve 42, pelvic nerve 40, and pudendal nerve 44.

Regardless, in some embodiments, the delivered electrical stimulation modulates muscle activity to treat, for example, stress incontinence, UUI and/or mixed incontinence.

Stimulation Elements and Lead Assemblies

The stimulation element 66 can assume various forms appropriate for applying electrical stimulation to the anatomical feature (e.g., nerve) of interest. For example, the stimulation element 66 can be formatted for targeting a sacral nerve via the sacral foramen (e.g., configured to be delivered percutaneously, optionally with fluoroscopy support). The stimulation element 66 can be or include one or more electrodes in the form of ring electrodes, segmented electrodes, and partial ring electrodes. In some examples, the example stimulation element(s) may be or include a cuff electrode, comprising at least some of substantially the same features and attributes as described in Bonde et al. U.S. Pat. No. 8,340,785, SELF EXPANDING ELECTRODE CUFF, issued on Dec. 25, 2102 and Bonde et al. U.S. Pat. No. 9,227,053, SELF EXPANDING ELECTRODE CUFF, issued on Jan. 5, 2016, both which are hereby incorporated by reference in their entirety. Moreover, in some examples a stimulation lead, which may comprise one example implementation of a stimulation element, may comprise at least some of substantially the same features and attributes as the stimulation lead described in U.S. Pat. No. 6,572,543 to Christopherson et al., and which is incorporated herein by reference in its entirety.

With optional embodiments in which the stimulation element 66 is or includes a cuff-type format, the stimulation element 66 can be configured to target nerves controlling the external urethral sphincter 34 and/or the external anal sphincter. In some embodiments, the stimulation element 66 is configured to target the external urethral sphincter 34 muscle directly, and can be delivered trans-urethrally in accordance with some methods of the present disclosure. With these and related embodiments, a design or form factor of the stimulation element 66 can be customized for the size of the external urethral sphincter 34 of an individual patient. The cuff format can wrap about the external urethral sphincter 34 muscle and then cause contraction thereof with electrical stimulation. Wrapping about the external urethral sphincter 34 muscle (and thus the urethra 14) can provide a highly viable target site that better ensures that terminal nerve branches will be available for stimulation. With these and other embodiments, the stimulation element 66 can be designed to include or incorporate an active and/or passive anchoring system (e.g., sutures, tines, etc.). With some optional systems and methods of the present disclosure, the stimulation element 66 is or includes a cuff electrode applying stimulation energy to a targeted nerve and affixed to the muscle at a location at which the targeted nerve innervates the muscle. With other optional systems and methods of the present disclosure, two or more cuff-type electrodes are provided, each electrically connected to the same IPG 64 (e.g., each of the two or more cuff-type electrodes are carried by a common lead body, or two or more of the cuff-type electrodes can be carried by separate lead bodies that are each connected to a separate port in the header of the IPG 64). With these and related embodiments, one cuff-type electrode can be implanted to affect or stimulate a first nerve and a second cuff-type electrode can be implanted to affect or stimulate a second nerve; alternatively, two or more cuff-type electrodes can be implanted along the same nerve, but at different branches thereof (e.g., upon final implant, the system can operate to stimulate multiple branches of the pudendal nerve with different cuff-type electrodes). In yet other embodiments, two or more non-cuff-type leads can be utilized, or a combination of one or more cuff-type leads and one or more non-cuff-type leads.

Other implantable stimulation element or electrode configurations appropriate for applying stimulation energy to a selected region or segment are also acceptable. For example, the stimulation element 66 can be provided as part of an electrode assembly configured to wrap partially or completely about the selected region or segment of a targeted nerve or anatomical feature. In other embodiments, the stimulation element 66 can be provided as part of an electrode assembly carrying a tissue fastener (e.g., a screw or similar mechanical coupling device or mechanism) formatted to be inserted or secured to tissue highly proximate the targeted nerve, nerve branch, or muscle.

With some example systems and method of the present disclosure, the stimulation element 66 is placed on an external plane of a targeted muscle to apply electrical stimulation to the targeted muscle and/or to a targeted nerve that innervates the muscle at the location of implant. For example, the stimulation element 66 can be delivered through a wall of the bladder 10, through the skin and onto the bladder 10 via an access location below the lowest rib.

In some embodiments, the stimulation element 66 is provided as an array of electrode contacts, with the electrodes of the array being selectively activated to produce a desired stimulation vector. For example, the electrode array can be a 3×3 array of electrode contacts, a 3×4 array of electrode contacts, etc. Each given stimulation element may comprise an array of electrically conductive elements (e.g. electrodes, electrode contacts, etc.), which may be arranged in in a wide variety of configurations, such as but not limited to a row, rows, staggered configurations, grid (2×2, 3×3), and combinations thereof. As is known in the art, different combinations of the electrode contacts can be activated. In another example, the stimulation element 66 can be provided as one of a series of ring electrodes spaced along a lead, with each of the ring electrodes being secured over the target site at spaced locations.

In some examples, the stimulation element(s) 66 can be electrically connected relative to a common element, such as the IPG 64 with such connective wires omitted for illustrative clarity or with such connection being wireless. In some instances, the example of connective wires may take the form of a lead for the stimulation element 66.

Figure 4A:
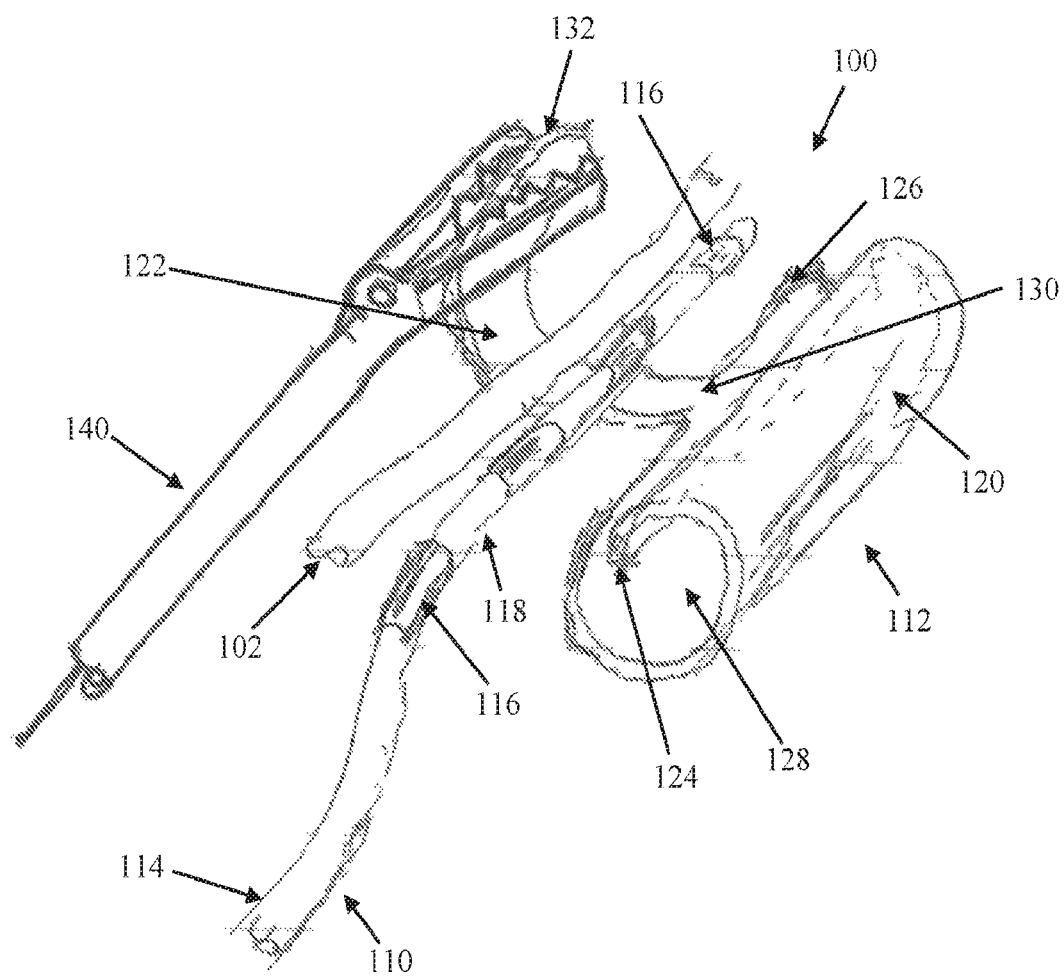
FIG. 4A is a simplified perspective view of a portion of a lead assembly useful with systems and methods of the present disclosure being applied to a nerve.

In some embodiments, the stimulation element(s) 66 Is provide as part of an electrode lead assembly adapted, for example, to be implanted percutaneously (e.g., via a laparoscopic approach). For example, FIG. 4A illustrates one non-limiting example of an electrode lead assembly 100 of the present disclosure being secured or implanted relative to a nerve 102 (e.g., the pudendal nerve). The lead assembly 100 includes a lead 110 and a cuff 112. The lead 110 can have a format and construction akin to conventional lead designs, including a lead body 114 carrying one or more stimulation elements or electrodes 116 (e.g., ring electrodes) along a distal region 118 thereof. Electrical connections or wiring (not shown) for each of the electrodes 116 is carried by lead body 114 in an electrically isolated fashion, with a proximal region (not shown) of the lead body 114 formatted for physical and electrical connection to an implantable pulse generator. Other lead constructions are also acceptable.

The cuff 112 includes a cuff body 120 and a strap 122. The cuff body 120 is formed of a soft, electrically non-conductive material appropriate for direct contact with a nerve; for example, the cuff body 120 can be silicone. The cuff body 120 is configured to self-assume or self-revert to the overlapping or wrapped shape reflected by FIG. 4A. The wrapped shape can include a first edge 124 located below or inside of an opposing second edge 126, with the cuff body 120 forming or defining a central passage 128. The passage 128 can be accessed via a gap between the opposing edges 124, 126. A fixed end 130 of the strap 122 is attached or connected to the cuff body 120 (e.g., at or adjacent the second edge 126), with the strap 122 extending from the cuff body 120 to a free end 132. The strap 122 is configured to self-assume or self-revert to a curved shape, effectively wrapping over or along an exterior of the cuff body 120 in a normal state (it being understood that FIG. 4A reflects the strap 122 in a deflected state). The strap 122 can be integrally formed with the cuff body 120, or can be separately formed and assembled to the cuff body 120. Regardless, the free end 132 of the strap 122 can be manipulated or deflected away from the cuff body 120 as shown in FIG. 4A, affording more direct access to, and perhaps enlarging, the gap between the cuff body edges 124, 126.

Figure 4B:
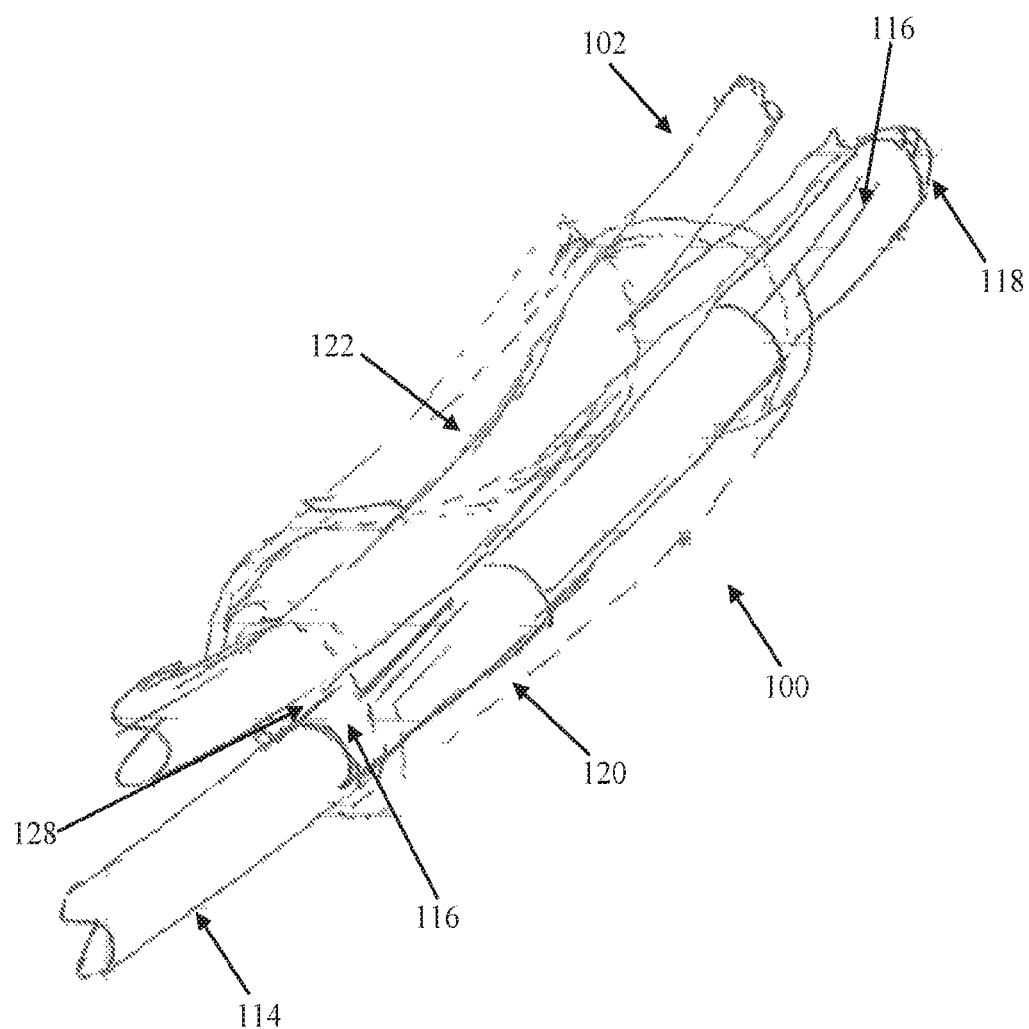
FIG. 4B is a simplified perspective view of the lead assembly of FIG. 4A upon final implant.

During an implantation procedure, the distal region 118 of the lead body 114 is delivered to the target site as shown, locating the electrodes 116 along or in close proximity to the nerve 102 of interest. The cuff 112 is similarly delivered to the target site (e.g., via a laparoscopic scope). The clinician uses a tool 140 (e.g., a laparoscopic grasper) to engage the strap 122 and manipulate the free end 132 away from the cuff body 120 as shown. The lead 110 and the nerve 102 can then readily be inserted between the cuff body edges 124, 126, and into the central passage 128. The strap 122 is then released from the tool 140, and self-reverts to a normal state in which the strap 122 wraps about the cuff body 120. FIG. 4B illustrates the lead assembly 100 upon final implant. The distal region 118 of the lead body 114 (and thus the electrodes 116) is retained against the nerve 102 within the central passage 128 (referenced generally), with the natural or normal overlapping or wrapped shape of the cuff body 120 and the strap 122 preventing the lead body 114 from becoming displaced relative to the nerve 102.

Some of the example stimulation element/lead assemblies of the present disclosure can assume other forms appropriate for percutaneous delivery/implantation to a location conducive to stimulating a desired nerve segment (e.g., the pudendal nerve) or other anatomy (e.g., direct muscle stimulation). For example, the percutaneous lead bodies of the present disclosure can optionally have an elongated, generally cylindrical shape and carry one or more stimulation elements (e.g., ring electrodes) at a distal region thereof. Further, some of the percutaneous lead assemblies of the present disclosure are configured to provide one or more of deployable fixation features, reversible (e.g., re-sheathable) fixation features, and bilateral stability fixation features. With these and related embodiments, the optional lead assemblies of the present disclosure can be useful, for example, with percutaneous delivery techniques for accessing and applying stimulating to the pudendal nerve. As a point of reference, the need for fixation of a percutaneously-delivered stimulation lead relative to the pudendal nerve can be different from that associated with a sacral foramen nerve. For example, a sacral foramen nerve stimulation lead assembly normally accounts for only retrograde expulsion (although antegrade migration may occasionally occur), whereas a percutaneous pudendal nerve stimulation lead assembly desirably provides bi-lateral fixation (resisting both retrograde and antegrade migration/expulsion).

Figure 5A:
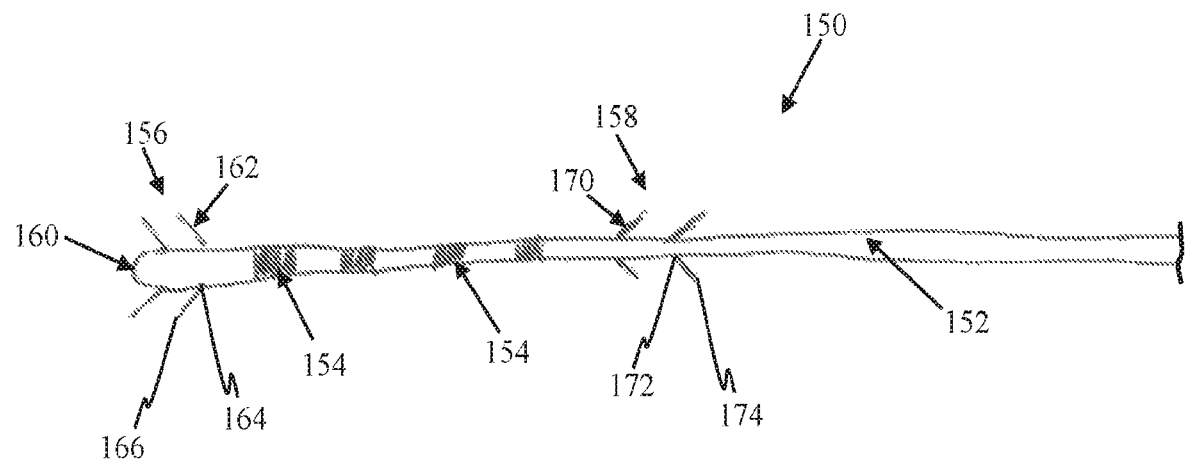
FIG. 5A is a simplified side view of a portion of a lead assembly useful with systems and methods of the present disclosure.

With the above in mind, a portion of one example of a lead assembly 150 useful with the devices, systems, and methods of the present disclosure, for example for percutaneous placement to apply stimulation to a pudendal nerve, is shown in FIG. 5A. The lead assembly 150 includes a cylindrical lead body 152, one or more simulation elements 154, a first fixation unit 156 (referenced generally), and a second fixation unit 158 (referenced generally). The lead body 152 can be of a type and construction conventionally employed with percutaneous stimulation leads, and extends from a distal end 160 to an opposing, proximal end (not shown). The stimulation element(s) 154 can also be of type and construction conventionally employed for delivering stimulation energy to a nerve or other anatomy, and in some embodiments can be a ring electrode, a partial ring electrode, etc. While FIG. 5A illustrates four stimulation elements 154, any other number, either greater or lesser, is equally acceptable. Regardless, the stimulation elements 154 are carried by the lead body 152 and are electrically connected to a respective conductor or wire within a thickness of the lead body 152 as is known in the art. A location of the stimulation elements 154 relative to a length of the lead body 152 can vary, but in general terms are located proximate the distal end 160.

The first fixation unit 156 is carried by or assembled to the lead body 152, and is located proximate the distal end 160. In some embodiments, the first fixation unit 156 is located between a distal-most one of the stimulation elements 154 and the distal end 160. The first fixation unit 156 includes or comprises one or more tines or anchors 162 that are configured to be deflectable from the arrangement of FIG. 5A under the influence of an external force, and to naturally self-assume or self-revert to the shape and/or orientation relative to the lead body 152 of FIG. 5A upon removal of the external force. In some embodiments, the tines 162 of the first fixation unit 156 are configured or formed relative to the lead body 152 to exhibit a distal bias. For example, each of the tines 162 defines a fixed end 164 opposite a free end 166 (labeled for one of the tines 162 in FIG. 5A). The fixed end 164 is attached or fixed to the lead body 152. In the normal state of FIG. 5A, extension of the tine 162 from the lead body 152 includes the free end 166 being radially spaced from the lead body 152, and the free end 166 being distally spaced (relative to a longitudinal direction of the lead body 152) from the fixed end 164. With this orientation or arrangement, following implant of the lead assembly 150 in which the free end 166 is in contact with or embedded within tissue of the patient, the tine 152 will overtly resist movement of the lead body 152 in the distal direction. The tine 162 can be deflected from the arrangement of FIG. 5A (for example during percutaneous delivery), forcing the free end 166 radially inwardly toward the lead body 152; upon removal of this force, the tine 162 will self-revert back to the orientation of FIG. 5A. The first fixation unit 156 can include any number of the tines 162, and the tines 162 can be uniformly or non-uniformly spaced relative to one another about a circumference of the lead body 152.

The second fixation unit 158 is carried by or assembled to the lead body 152, and is located proximal the stimulation element(s) 154. In some embodiments, the second fixation unit 158 is located proximate, but proximally spaced from, a proximal-most one of the stimulation elements 154. The second fixation unit 158 includes or comprises one or more tines or anchors 170 that are configured to be deflectable from the arrangement of FIG. 5A under the influence of an external force, and optionally to naturally self-assume or self-revert to the shape and/or orientation relative to the lead body 152 of FIG. 5A upon removal of the external force. In some embodiments, the tines 170 of the second fixation unit 158 are configured or formed relative to the lead body 152 to exhibit a proximal bias. For example, each of the tines 170 defines a fixed end 172 opposite a free end 174 (labeled for one of the tines 170 in FIG. 5A). The fixed end 172 is attached or fixed to the lead body 152. In the normal state of FIG. 5A, extension of the tine 170 from the lead body 152 includes the free end 174 being radially spaced from the lead body 152, and the free end 174 being proximally spaced (relative to a longitudinal direction of the lead body 152) from the fixed end 172. With this orientation or arrangement, following implant of the lead assembly 150 in which the free end 174 is in contact with or embedded within tissue of the patient, the tine 170 will overtly resist movement of the lead body 152 in the proximal direction. The tine 170 can be deflected from the arrangement of FIG. 5A (for example during percutaneous delivery), forcing the free end 174 radially inwardly toward the lead body 152; upon removal of this force, the tine 170 will self-revert back to the orientation of FIG. 5A. The second fixation unit 158 can include any number of the tines 170, and the tines 170 can be uniformly or non-uniformly spaced relative to one another about a circumference of the lead body 152. While the tines 162, 170 have been described as being configured to self-deploy, in other embodiments one or more of the tines 162, 170 can be configured to achieve the deployed arrangement in response to an operator's action (e.g., insertion or rotation of a steering stylet).

Figure 5B:
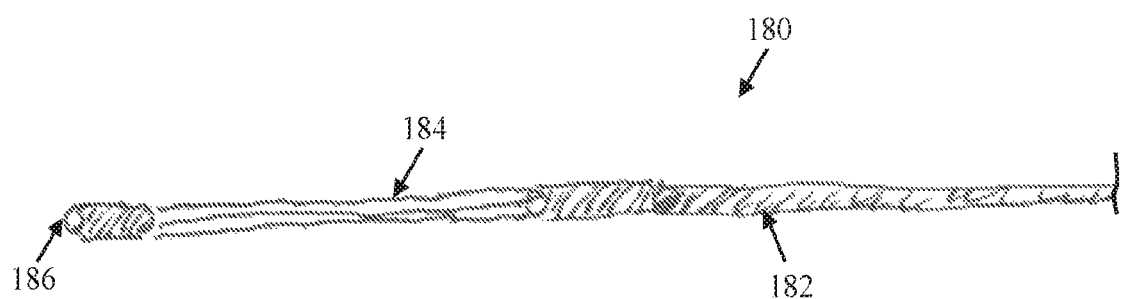
FIG. 5B is a simplified side view of a delivery tool useful with the lead assembly of FIG. 5A.

From the above explanations, the first and second fixation units 156, 158 combine to provide the lead assembly 150 with bi-lateral fixation, resisting retrograde and antegrade migration upon final implant. Various tools can be employed to assist with the delivery (e.g., percutaneous delivery) of the lead assembly 150 to a desired target site (e.g., the stimulation element(s) being located in close proximity to a desired segment of a targeted nerve, such as the pudendal nerve). For example, a delivery tool 180 useful with the lead assembly 150 is shown in FIG. 5B. The delivery tool 180 includes a sheath 182 extending from a handle 184. The sheath 182 can assume various forms known in the art, and defines an inner diameter approximating an outer diameter of the lead body 152. Thus, the lead body 152 can be slidably received within the sheath 182, with a hoop strength of the sheath 182 being appropriate to deflect and hold each of the tines 162, 170 against the lead body 152, generating a low delivery profile. Further, the sheath 182 covers the tines 162, 170 during delivery, preventing inadvertent contact between the tines 162, 170 and tissue. Once the lead body 152 has been positioned at a desired location, the sheath 182 is proximally withdrawn, allowing the tines 162, 170 to self-revert to the arrangement of FIG. 5A, engaging with tissue to limit or prevent migration. Notably, the sheath 182 can readily be re-advanced over at least the tines 162 of the first fixation unit to effect re-sheathing when desired.

In some embodiments, the delivery tool 180 can optionally incorporate features that facilitate testing of the stimulation element(s) 154 with the sheath 182 in place over the lead assembly 150. For example, the sheath 182 can include or incorporate one or more windows 184. A size and longitudinal location of the window(s) 184 relative to a distal end 186 of the sheath 182 corresponds with one or more of the stimulation elements 154 relative to the distal end 160. With this construction, when the sheath 182 is arranged over the lead body 152 with the distal end 186 of the sheath 182 proximate or in contact with the distal end 160 of the lead body 152, one or more of the stimulation elements 154 are exposed within or at the window 184 while the tines 162, 170 remain covered by the sheath 182. During an implantation or delivery procedure, the combination lead assembly 150/sheath 182 can be directed to an approximate target site. Once at the approximated location and prior to removal of the sheath 182, an arrangement of the stimulation element(s) 154 relative to targeted anatomy (e.g., a nerve segment) can be tested. For example, stimulation energy can be delivered to the stimulation element(s) 154; because the stimulation element(s) 154 are exposed at the window(s) 184, the exposed stimulation element(s) 154 apply the energy to the patient's anatomy. The clinician can observe the effect(s) of the so-applied stimulation energy and evaluate a location of the stimulation element(s) 154 relative to desired anatomy. As a result of this evaluation, the clinician may decide to reposition the lead body 152 and repeat the testing protocol. Once the clinician is satisfied with the location of the lead body 152 (and in particular the stimulation element(s) 154), the sheath 182 is removed and the implantation procedure completed.

Figure 6A:
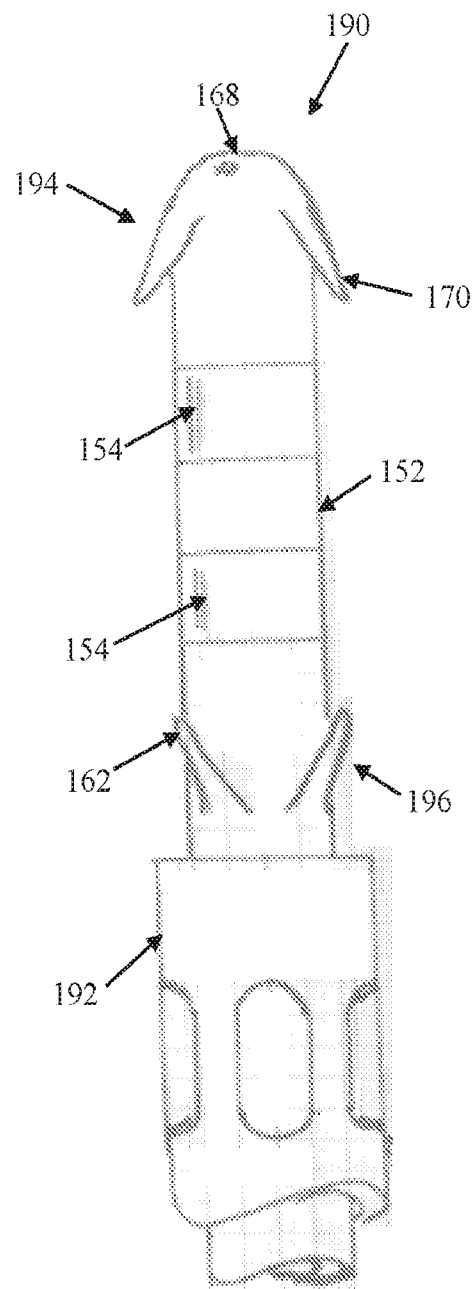
FIG. 6A is a simplified, side perspective view of a portion of lead assembly useful with the systems and methods of the present disclosure in a deployed state, along with a delivery sheath.
Figure 6B:
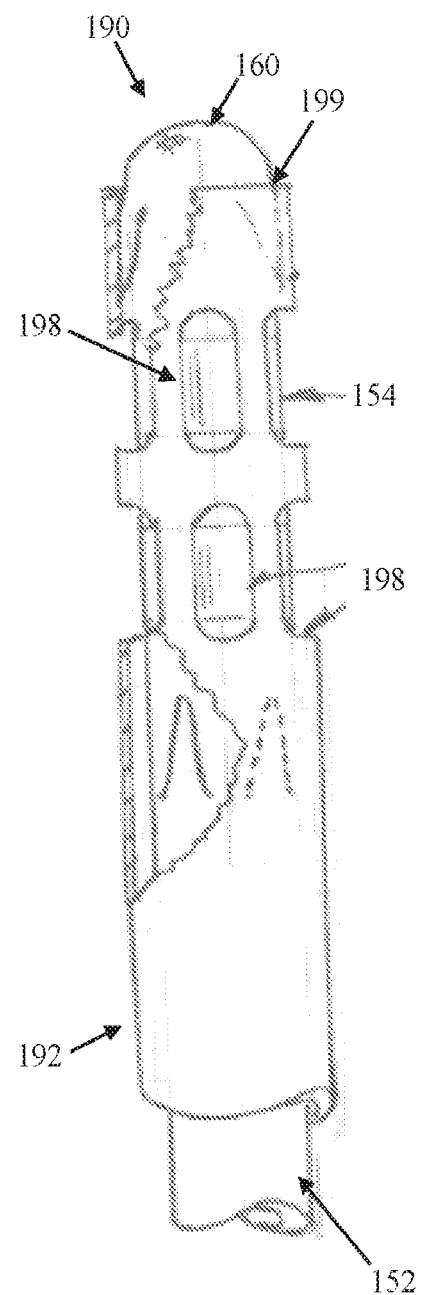
FIG. 6B is a simplified, side perspective view of the lead assembly and sheath of FIG. 6A arranged in a delivery state.

While the lead assembly 150 has been shown and described as providing or including the distally-biased tines 162 proximate the distal end 160 of the lead body 152, and the proximally-biased tines 170 proximal the stimulation elements 154, other constructions are also acceptable. For example, a portion of another example of a lead assembly 190 useful with the devices, systems, and methods of the present disclosure, for example for percutaneous placement to apply stimulation to a pudendal nerve, is shown in FIG. 6A, along with a sheath 192. The lead assembly 190 includes the cylindrical lead body 152 and the stimulation elements 154 as described above, along with a first fixation unit 194 and a second fixation unit 196. The first fixation unit 194 is located proximate the distal end 160 of the lead body 152, and includes one or more of the proximally-biased tines 170. The second fixation unit 196 is located adjacent to, but proximal of, a proximal-most one of the stimulation elements 154, and includes one or more of the distally-biased tines 162.

Where provided, the sheath 192 can assist in the delivery of the lead assembly 190 to a target site. For example, and as shown in FIG. 6B, prior to a delivery procedure, the sheath 192 can be distally advanced over the lead assembly 190, forcing or compressing the tines 162, 170 against the lead body 152 and creating a low delivery profile. The tines 162, 170 remain covered by the sheath 192 during delivery, preventing inadvertent contact between the tines 162, 170 and tissue. Once the lead body 152 has been positioned at a desired location, the sheath 192 is proximally withdrawn, allowing the tines 162, 170 to self-revert to the arrangement of FIG. 6A, engaging with tissue to limit or prevent migration. By providing proximally-biased and distally-biased tines, the lead assembly 190 has bi-lateral fixation.

In some embodiments, the sheath 192 can include or incorporate one or more windows 198. A size and longitudinal location of the window(s) 198 relative to a distal end 199 of the sheath 192 corresponds with one or more of the stimulation elements 154 relative to the distal end 160 of the lead body 152. With this construction, when the sheath 192 is arranged over the lead body 152 with the distal end 199 of the sheath 192 proximate or in contact with the distal end 160 of the lead body 152, the stimulation elements 154 are exposed within or at a corresponding one of the windows 198 while the tines 162, 170 remain covered by the sheath 192. The arrangement of FIG. 6B allows a clinician to perform stimulation testing/lead placement evaluation as described prior to deployment of the tines 162, 170.

Figure 7A:
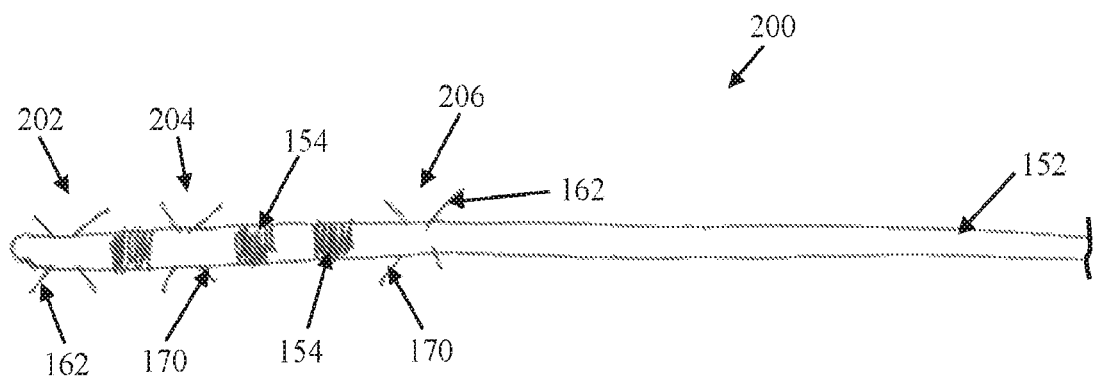
FIG. 7A is a simplified side view of a portion of a lead assembly useful with systems and methods of the present disclosure.

A portion of another example of a lead assembly 200 useful with the devices, systems, and methods of the present disclosure, for example for percutaneous placement to apply stimulation to a pudendal nerve, is shown in FIG. 7A. The lead assembly 200 includes the cylindrical lead body 152 and the simulation elements 154 as described above, along with a first fixation unit 202, a second fixation unit 204, and a third fixation unit 206. The first fixation unit 202 is located along the lead body 152 between the distal end 160 and a distal-most one of the stimulation elements 154. The second fixation unit 204 is located along the lead body 152 between neighboring ones of the stimulation elements 154. The third fixation unit 206 is located along the lead body 152 adjacent, but proximal of, a proximal-most one of the stimulation elements 154. The fixation units 202-206 can be akin to the descriptions above, and include one or more tines or anchors. In some examples, each of the fixation units 202-206 can include a combination of the distally-biased tines 162 and the proximally-biased tines 170. Regardless, the fixation units 202-206 alone or in combination provide the bi-lateral fixation attributes described above.

Various tools can be employed to assist with the delivery (e.g., percutaneous delivery) of the lead assembly 200 to a desired target site (e.g., the stimulation element(s) being located in close proximity to a desired segment of a targeted nerve, such as the pudendal nerve). For example, a delivery tool akin to the delivery tool 180 described above can be employed. The sheath of a delivery tool useful with the lead assembly 200 can form or define two or more spaced apart windows such that when loaded over the lead assembly 200, the stimulation elements 154 are exposed at the windows while the tines 162, 170 of the fixation units 202-206 remain covered.

Figure 7B:
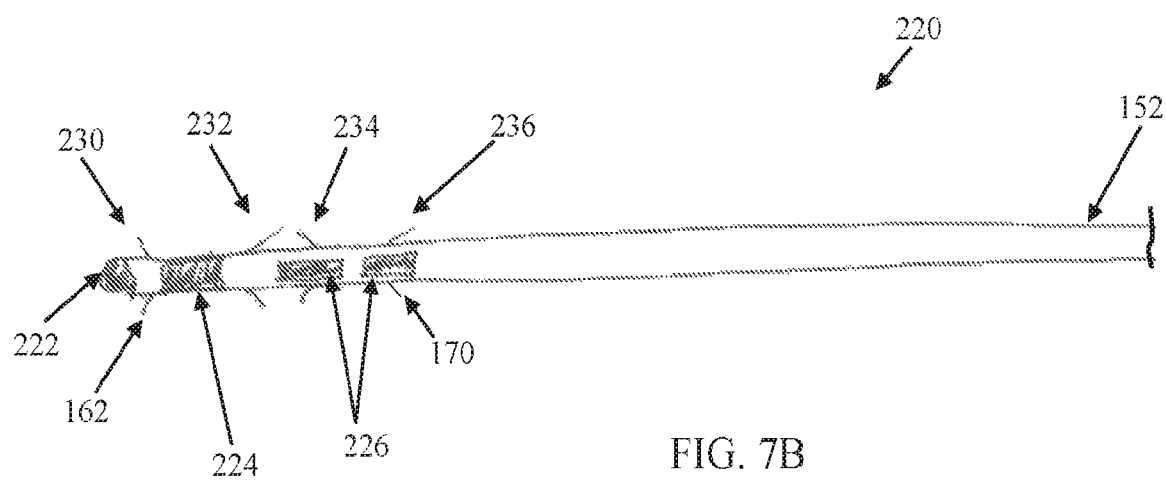
FIG. 7B is a simplified side view of a portion of a lead assembly useful with systems and methods of the present disclosure.

A portion of another example of a lead assembly 220 useful with the devices, systems, and methods of the present disclosure, for example for percutaneous placement to apply stimulation to a pudendal nerve, is shown in FIG. 7B. The lead assembly 220 includes the cylindrical lead body 152 as described above, various stimulation elements, such as a tip electrode 222, one or more ring electrodes 224, and one or more partial or segmented electrodes 226, a first fixation unit 230, a second fixation unit 232, a third fixation unit 234, and a fourth fixation unit 236. The first fixation unit 230 is located along the lead body 152 proximate the distal end, for example between the tip electrode 222 and neighboring stimulation element, such as the ring electrode 224. The second fixation unit 232 is located along the lead body 152 between neighboring ones of the stimulation elements, such as between the ring electrode and a distal-most one of the segmented electrodes 226. The third and fourth fixation units 234, 236 are located along the lead body 152 so as to be aligned with a corresponding one of the segmented electrodes 226. The fixation units 230-236 can be akin to the descriptions above, and include one or more tines or anchors. In some examples, each of the fixation units 230-236 can include a combination of the distally-biased tines 162 and the proximally-biased tines 170 (several of which are labeled in the view). In other examples, the first and third fixation units 230, 234 can include the distally biased tines 162, and the second and fourth fixation units 232, 236 can include the proximally-biased tines 170. Regardless, the fixation units 230-236 alone or in combination provide the bi-lateral fixation attributes described above.

Various tools can be employed to assist with the delivery (e.g., percutaneous delivery) of the lead assembly 220 to a desired target site (e.g., the stimulation element(s) being located in close proximity to a desired segment of a targeted nerve, such as the pudendal nerve). For example, a delivery tool akin to the delivery tool 180 described above can be employed. The sheath of a delivery tool useful with the lead assembly 220 can form or define two or more spaced apart windows such that when loaded over the lead assembly 220, one or more of the stimulation elements (e.g., one or more of the tip electrode 222, ring electrodes 224, and/or segmented electrodes 226) are exposed at the windows while the tines 162, 170 of the fixation units 230-236 remain covered.

Figure 8A:
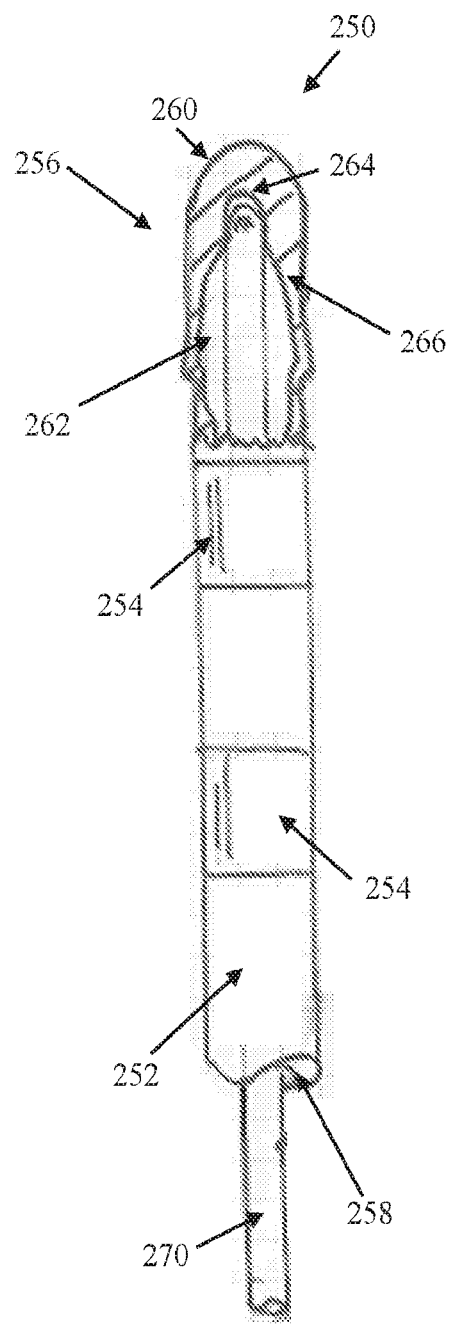
FIG. 8A is a simplified, side perspective view of a portion of lead assembly useful with the systems and methods of the present disclosure in a delivery state, along with a stylet.
Figure 8B:
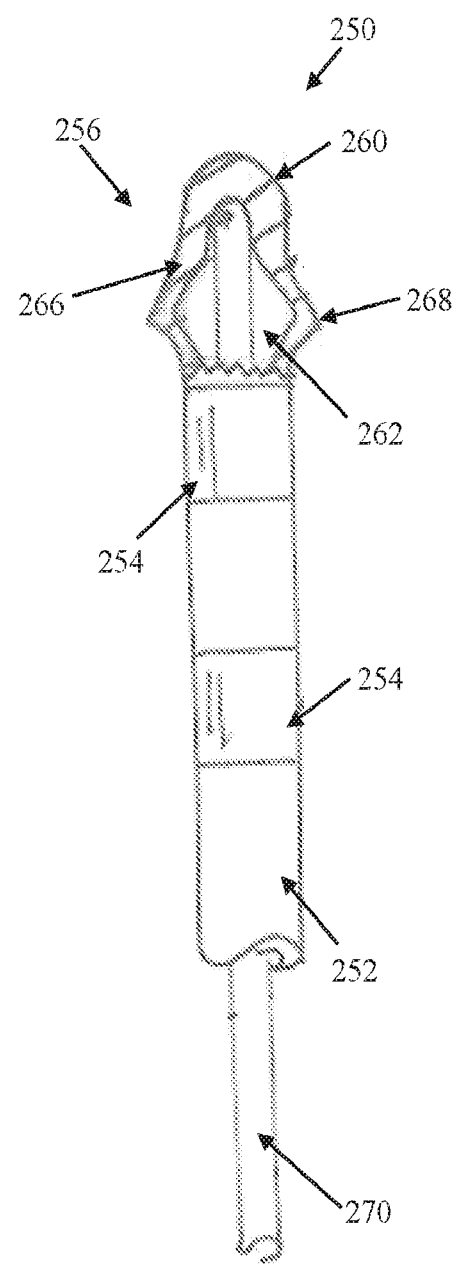
FIG. 8B is a simplified, side perspective view of the lead assembly and stylet of FIG. 8A arranged in a deployed state.

A portion of another example of a lead assembly 250 useful with the devices, systems, and methods of the present disclosure, for example for percutaneous placement to apply stimulation to a pudendal nerve, is shown in FIGS. 8A and 8B. The lead assembly 250 includes a cylindrical lead body 252, one or more stimulation elements 254, and a fixation unit 256. The lead body 252 can assume any of the types known in the art, and defines a lumen 258 (referenced generally). The stimulation element(s) 254 can also be of type and construction conventionally employed for delivering stimulation energy to a nerve or other anatomy, and in some embodiments can be a ring electrode, a partial ring electrode, etc. While FIGS. 8A and 8B illustrates two stimulation elements 254, any other number, either greater or lesser, is equally acceptable. Regardless, the stimulation elements 254 are carried by the lead body 252 and are electrically connected to a respective conductor or wire within a thickness of the lead body 252 as is known in the art.

The fixation unit 256 can include a fixation body 260 formed by or assembled to the lead body 252, This fixation body 260 serves as a distal tip of the lead assembly 250 and defines a chamber 262 terminating at a groove 264. The chamber 262 is open to, or is a continuation of, the lumen 258. The fixation body 260 can be formed of an elastic or similar material configured to self-assume or self-deflect to the predetermined, normal or natural shape in the free state of FIG. 8B. The predetermined shape is characterized by a side or sidewall 266 of the fixation body 260 forming one or more radially-outward projections 268. For example, a radius of the radially-outward projection(s) 268 relative to a centerline of the lead body 252 is greater than an outer radius of the lead body 252. In some embodiments, a radially-outermost extent of the projection(s) 268 can form an edge or corner or other feature conducive to engaging tissue.

As reflected by FIG. 8A, the fixation body 260 is configured to be readily forced to an elongated shape in which the sidewall 266 is relatively straight and the radially-outward projections 268 are minimized or removed or collapsed. Upon removal of the elongation force, the fixation body 260 self-reverts back to the natural shape of FIG. 8B. For example, a stylet or rod 270 can be slidably inserted into the lumen 258, and a distal end 272 thereof located in the groove 264. With further distal advancement of the stylet 270 while the lead assembly 250 is held stationary, or vice-versa, the stylet 270 forces the fixation body 260 to the elongated shape as in FIG. 8A. In this arrangement, the lead assembly 250 has a streamlined shape (e.g., the radially-outward projections 268 do not exists or are minimal) conducive to percutaneous delivery. Once the lead body 250, and in particular the stimulation elements 254, is located at a desired target site (e.g., following testing of the stimulation elements 254), the stylet 270 is removed, allowing the fixation body 260 to revert back to or towards the natural shape. With this transition, the radially-outward projection(s) 268 will engage surrounding tissue, providing fixation of the lead assembly 250 relative to the patient's anatomy at the target site. Under circumstances where re-positioning or removal of the lead assembly 250 is desired, the stylet 270 can be inserted into the lumen 258 and manipulated to force the fixation body 260 to the elongated shape of FIG. 8A; with this arrangement, engagement of the fixation body 260 with surrounding tissue is greatly reduced or eliminated, allowing the lead assembly 250 to easily move relative to the patient's anatomy.

Figure 9A:
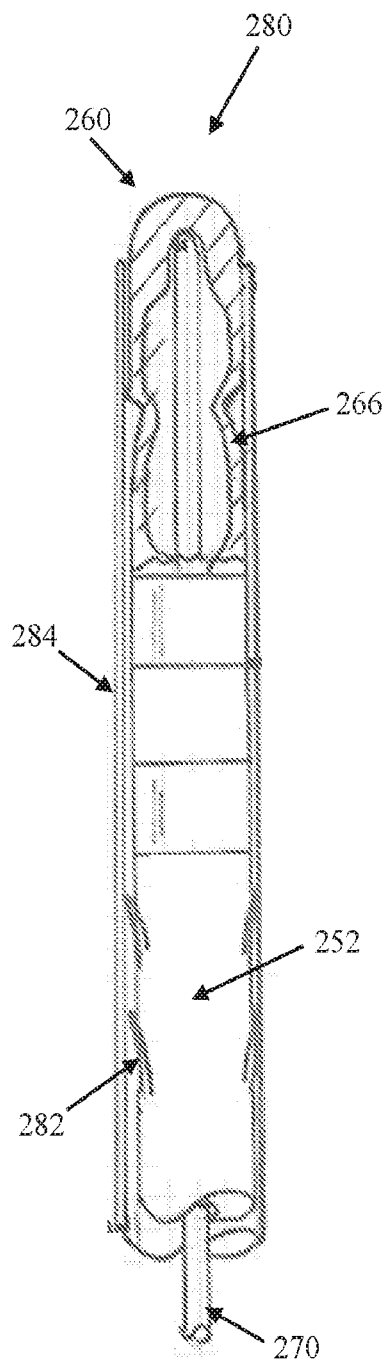
FIG. 9A is a simplified, side perspective view of a portion of lead assembly useful with the systems and methods of the present disclosure in a delivery state, along with a sheath and a stylet.
Figure 9B:
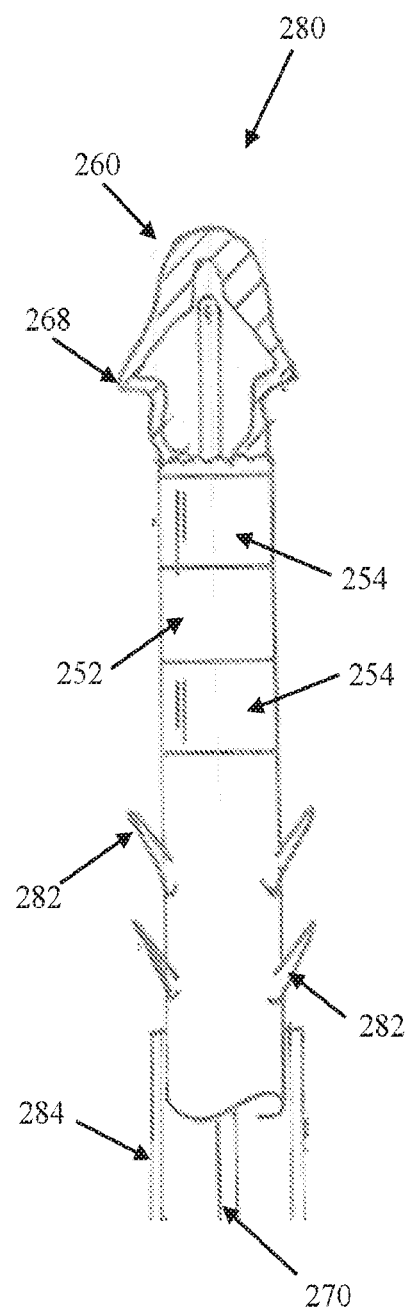
FIG. 9B is a simplified, side perspective view of the lead assembly, sheath and stylet of FIG. 9A arranged in a deployed state.

Though not shown, the lead assembly 250 can optionally include additional fixation elements (e.g., tines, anchors, etc.) proximal the stimulation elements 254. With this in mind, a portion of another example of a lead assembly 280 useful with the devices, systems, and methods of the present disclosure is shown in FIGS. 9A and 9B. The lead assembly 280 includes the lead body 252, the stimulation element(s) 254, and the fixation body 260 as described above, along with one more tines or anchors 282. The tine(s) 282 can be located along the lead body 252 adjacent to, but proximal of, the stimulation element(s) 254, and can have any of the forms described above. In some embodiments, one or more or all of the tines 282 can have or exhibit a distal bias as described above, and can be configured to self-revert from a collapsed state to or toward the arrangement of FIG. 9B. In other embodiments, the tines 282 can be configured to achieve the deployed state or shape in response to operator action.

As reflected by FIG. 9A, the fixation body 260 is configured to be readily forced to an elongated shape in which the sidewall 266 is relatively straight and the radially-outward projections 268 are minimized or removed or collapsed as described above. Collapsing of the fixation body 260 can be facilitated by the stylet 270 and/or by a sheath 284 slidably disposed over the lead assembly 280. Regardless, the sheath 284 can further temporarily force the tine(s) 282 to a collapsed state against the lead body 252. In some examples, the lead assembly 280 can be prepared for delivery to a target site by first forcing the fixation body 260 to the elongate shape of FIG. 9A with the stylet 270, and advancing the sheath 284 over the lead assembly 280 to collapse the tines 282. With this arrangement, the lead assembly 280/sheath 284 has a streamlined shape conducive to percutaneous delivery. In this state, the lead assembly 280 can be advanced to an approximate target site. Where desired, a location of the stimulation element(s) 254 relative to desired anatomy (e.g., nerve segment) can be tested, for example by first retracting the sheath 284 proximally beyond the stimulation element(s) (but still over the tines 282) and applying stimulation energy thereto. Once the lead body 252, and in particular the stimulation elements 254, are located at a desired target site, the stylet 270 and the sheath 284 are removed, allowing the fixation body 260 and the tines 282 to revert back to or towards their natural shapes. With this transition, the radially-outward projection(s) 268 and the tines 282 will engage surrounding tissue, providing fixation of the lead assembly 280 relative to the patient's anatomy at the target site. In some embodiments, the fixation body 260 more readily resists retrograde migration and the tines 282 resist antegrade migration, collectively providing the lead assembly with bi-lateral fixation. Under circumstances where re-positioning or removal of the lead assembly 280 is desired, the stylet 270 can be inserted into the lumen 258 and manipulated to force the fixation body 260 to the elongated shape of FIG. 9A; further, the sheath 284 can readily be advanced over the tines 282 (and optionally fixation body 260). With this arrangement, engagement of the fixation body 260 and the tines 282 with surrounding tissue is greatly reduced or eliminated, allowing the lead assembly 280 to easily move relative to the patient's anatomy.

A portion of another example of a lead assembly 300 useful with the devices, systems, and methods of the present disclosure, for example for percutaneous placement to apply stimulation to a pudendal nerve, is shown in FIGS. 10A and 10B. The lead assembly 300 includes the lead body 252, and the stimulation element(s) 254 as described above, along with a fixation unit 302.

The fixation unit 302 includes a fixation body 304 and a line 306. The fixation body 304 defines a chamber 308, and is formed of a material that self-retains a set shape. For example, the fixation body 304 can be forced from the elongated or "straight" shape of FIG. 10A to the deployed shape of FIG. 10B, and optionally will self-retain the so-imparted deployed shape. In some embodiments, the fixation body 304 can be an elastic material configured to self-retain the deployed shape of FIG. 10B. In other embodiments, the deployed shape of FIG. 10B can be pre-set into the fixation body 304, with the fixation body 304 being configured to self-revert to the deployed shape. The deployed shape is characterized by a side or sidewall 310 of the fixation body 304 forming one or more radially-outward projections 312. In other embodiments, the fixation unit 302 is configured such that the line 306 assists in maintaining the fixation body 304 in the deployed shape as described below. In some embodiments, ribs 314 or the like can be formed by or assembled to the fixation body 304 that can one or both of provide enhanced tissue engagement and support of the fixation body 304 in the deployed shape.

The line 306 can be a wire, strand, thread, etc., connected to a thickness of the fixation body 304 distal the chamber 308. For example, the line 306 can be threaded or looped through an aperture 316 in the fixation body 304. In other embodiments, the line 306 can be more permanently affixed to fixation body 304. Regardless, the line 306 extends proximally from the fixation body 304 along the lead body 252 (e.g., the lead body 252 can form a separate lumen for the line 306) to a proximal end thereof. A proximal end of the line 306 can extend proximally beyond the lead body 252 for grasping by a user, or can be connected to an actuator or similar device/mechanism adapted for facilitating the application/removal of a user-applied tensioning force onto the line 306.

As reflected by FIG. 10A, the fixation body 304 is configured to be readily forced to an elongated shape in which the sidewall 310 is relatively straight and the radially-outward projections 312 (FIG. 10B) are minimized or removed or collapsed. For example, the stylet 270 can be inserted into the fixation body 304 and manipulated to "straighten" the fixation body 304 commensurate with the descriptions above for delivery to a target site. Upon removal of the elongation force, the fixation body 304 can be forced to and/or self-reverts back to the deployed shape of FIG. 10B. For example, the line 306 can be pulled or tensioned, forcing the fixation body 304 to the deployed shape. With embodiments in which the fixation body 304 self-retains the deployed shape, the line 306 optionally can then be removed. In other embodiments, the line 306 can be held or locked relative to the lead body 252 under tension, serving to maintain the fixation body 304 in the deployed shape. Regardless, in the deployed shape, the radially-outward projection(s) 312 will engage surrounding tissue, providing fixation of the lead assembly 300 relative to the patient's anatomy at the target site. Under circumstances where re-positioning or removal of the lead assembly 300 is desired, tension in the line 306 (if still present) in removed and the stylet 270 can be inserted into the lumen 258 and manipulated to force the fixation body 306 to the elongated shape of FIG. 10A; with this arrangement, engagement of the fixation body 306 with surrounding tissue is greatly reduced or eliminated, allowing the lead assembly 300 to easily move relative to the patient's anatomy.

Figure 11A:
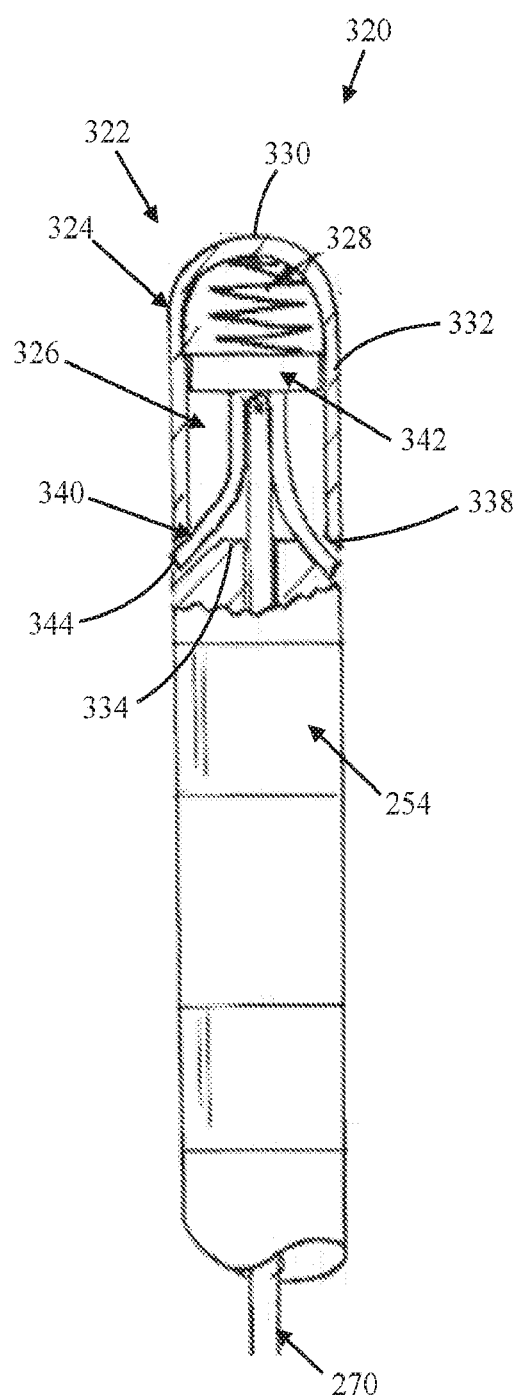
FIG. 11A is a simplified, side perspective view of a portion of lead assembly useful with the systems and methods of the present disclosure in a delivery state, along with a stylet.
Figure 11B:
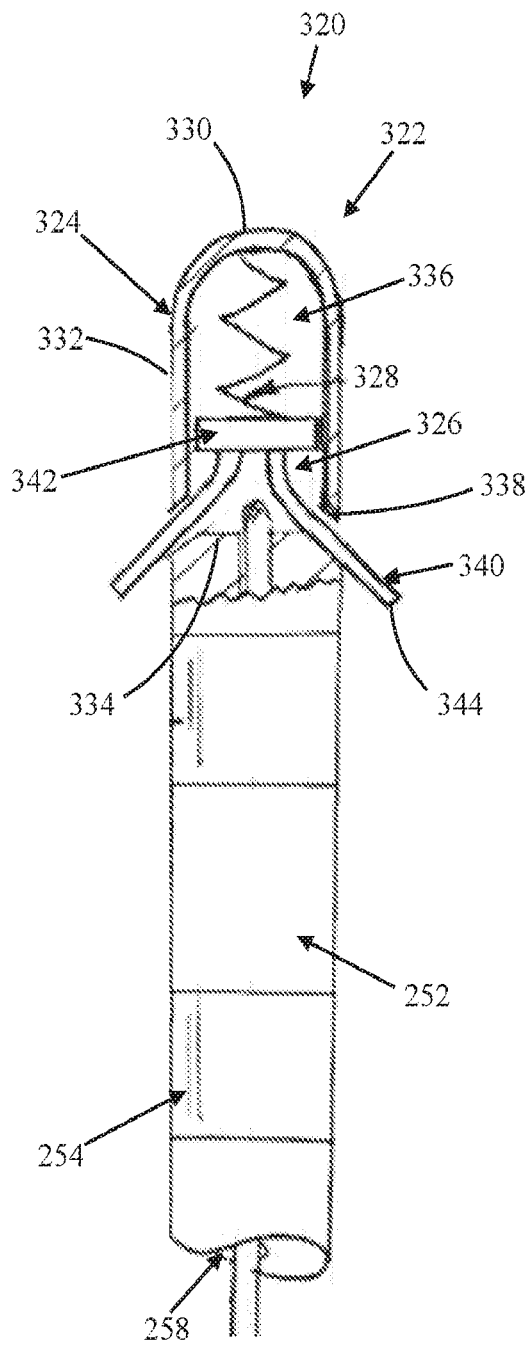
FIG. 11B is a simplified, side perspective view of the lead assembly and stylet of FIG. 11A arranged in a deployed state.

A portion of another example of a lead assembly 320 useful with the devices, systems, and methods of the present disclosure, for example for percutaneous placement to apply stimulation to a pudendal nerve, is shown in FIGS. 11A and 11B. The lead assembly 320 includes the lead body 252, and the stimulation element(s) 254 as described above, along with a fixation unit 322.

The fixation unit 322 includes a housing 324, a tine assembly 326, and a biasing member 328. The housing 324 can be formed by or assembled to the lead body 252, and serves as a distal tip of the lead assembly 320. The housing 324 includes or defines an end wall 330, a sidewall 332, an internal wall 334, and a chamber 336 that is open to the lumen 258. One or more passages 338 are formed through the sidewall 332 proximate the internal wall 334 for reasons made clear below. In some embodiments, a shape of each of the passages 338 has a proximal component in extension from the chamber 336 to an exterior of the housing 324 (e.g., an internal end of the passage 338 at the chamber 336 is distal an opposite, external end at the exterior of the sidewall 332).

The tine assembly 326 can assume a variety of forms, and in some embodiments includes one or more tines 340 and a base 342. The tines 340 each extend from a fixed end attached to or formed by the base 342 to a free end 344 opposite the base 342. The tines 340 can be formed of a rigid yet deformable material appropriate for engaging tissue, such as a mono-filament polymer body. The base 342 is sized and shaped to be slidably disposed within the chamber 336. Upon final construction, the tine assembly 326 is arranged relative to the housing 324 such that base 342 is within the chamber 336, and each of the tines 340 is aligned with a corresponding one of the passages 338.

The biasing member 328 can assume various forms appropriate for applying a force onto the base 342, and in some embodiments is or includes a spring or spring-like body. The biasing member 328 is arranged between and contacts the end wall 330 and the base 342. With this construction, the biasing member 328 applies a force onto the base 342 in the proximal direction (forcing the base 342 away from the end wall 330).

In the normal or deployed state of FIG. 11B, each of the tines 340 project through the corresponding passage 338, with the corresponding free end 344 being located radially outward of the lead body 252. A shape of the passages 338 optionally imparts a proximal bias into each of the tines 340 (e.g., the free end 344 is proximal a point of departure of the tine 340 from the housing 324).

As reflected by FIG. 11A, the fixation unit 322 is configured to be readily forced to a streamlined or delivery state in which the tines 340 are partially or completely retracted within the housing 324. For example, the stylet or rod 270 can be slidably inserted into the lumen 258, and the distal end 272 placed in contact with the base 342. With further distal advancement of the stylet 270 while the lead assembly 320 is held stationary, or vice-versa, a force applied by the stylet 270 onto the base 342 overcomes the force of the biasing member 328, causing the base 342 to move distally. Distal movement of the base 342, in turn, is transferred onto the tines 340, thus retracting the tines 340 into the housing 324. In this arrangement, the fixation unit 322 is streamlined (e.g., the tines 340 minimally project beyond the housing 324, if at all) conducive to percutaneous delivery. Once the lead assembly 320, and in particular the stimulation elements 254, is located at a desired target site (e.g., following testing of the stimulation elements 254), the stylet 270 is removed, allowing the biasing member 328 to force the base 342, and thus the tines 340, to or towards the arrangement of FIG. 11B. In other embodiments, a pull-wire can actively deploy the tines 340 without the need for a passive spring mechanism (e.g., the stylet 270 can push the tine assembly 326 in the opposite direction, retracting the tines 340 for removal or repositioning). In the deployed state, the tines 340 will engage surrounding tissue, providing fixation of the lead assembly 320 relative to the patient's anatomy at the target site. Under circumstances where re-positioning or removal of the lead assembly 320 is desired, the stylet 270 can be inserted into the lumen 258 and manipulated to force the base 342 to the arrangement of FIG. 11A, thus retracting the tines 340; with this arrangement, engagement of the tines 340 with surrounding tissue is greatly reduced or eliminated, allowing the lead assembly 320 to easily move relative to the patient's anatomy.

Returning to FIGS. 1-3, in some example embodiments, the stimulation element 66 can be provided as part of a cylindrical-type lead configured for placement in the periurethral space. For example, some systems and methods of the present disclosure can include transperineal placement of a cylindrical lead in the periurethral space for direct muscle stimulation of the pelvic floor muscles 18 and/or the external urethral sphincter 34 or other muscles (smooth) of the urethra 14 or bladder 10. Such systems and methods can further operate to stimulate the distal branches or terminal fibers of the pudendal nerve 44. In other, related embodiments, one or more cuff-type electrodes can be delivered via a transperineal approach for placement about or around the distal branches of the pudendal nerve 44. In yet other related embodiments, intramuscular-type electrodes are employed and are delivered via a transperineal approach.

As mentioned above, while a single stimulation element 66 is shown in FIG. 3, in other embodiments, two or three or more of the stimulation elements 66 can be provided, and may or may not have differing formats (or stimulation element components). Thus, one or two or three or more of any of the stimulation arrangements of the present disclosure can be provided with the treatment system for an individual patient. Two or three or more of the various non-limiting examples of stimulation element locations and formats provided in the present disclosure can be combined with a treatment system for an individual patient. For example, some treatment systems of the present disclosure are configured and formatted/programmed to provide stimulation to two or three or more target sites By way of non-limiting example, stimulation can be provided to certain target site(s) intended to treat incontinence when voiding/leakage is not desired, and stimulation to one or more other target site(s) intended to encourage or promote voiding (while at the same time not stimulating target sites otherwise intended to treat incontinence) when voiding is desired. With these and related embodiments, for example, efferent stimulation can be provided to at least one of the multiple target sites, whereas afferent stimulation can be provided to at least another one of the multiple target sites. In yet other embodiments, a single stimulation element 66 can be applied to a nerve that innervates two or more different target muscles or organs; under these circumstances, the systems and methods of the present disclosure can include applying a first stimulation signal format to the nerve to affect a first one of the targeted muscles or organs, and a second stimulation signal format to the nerve to affect a second one of the targeted muscles or organs.

Figure 12:
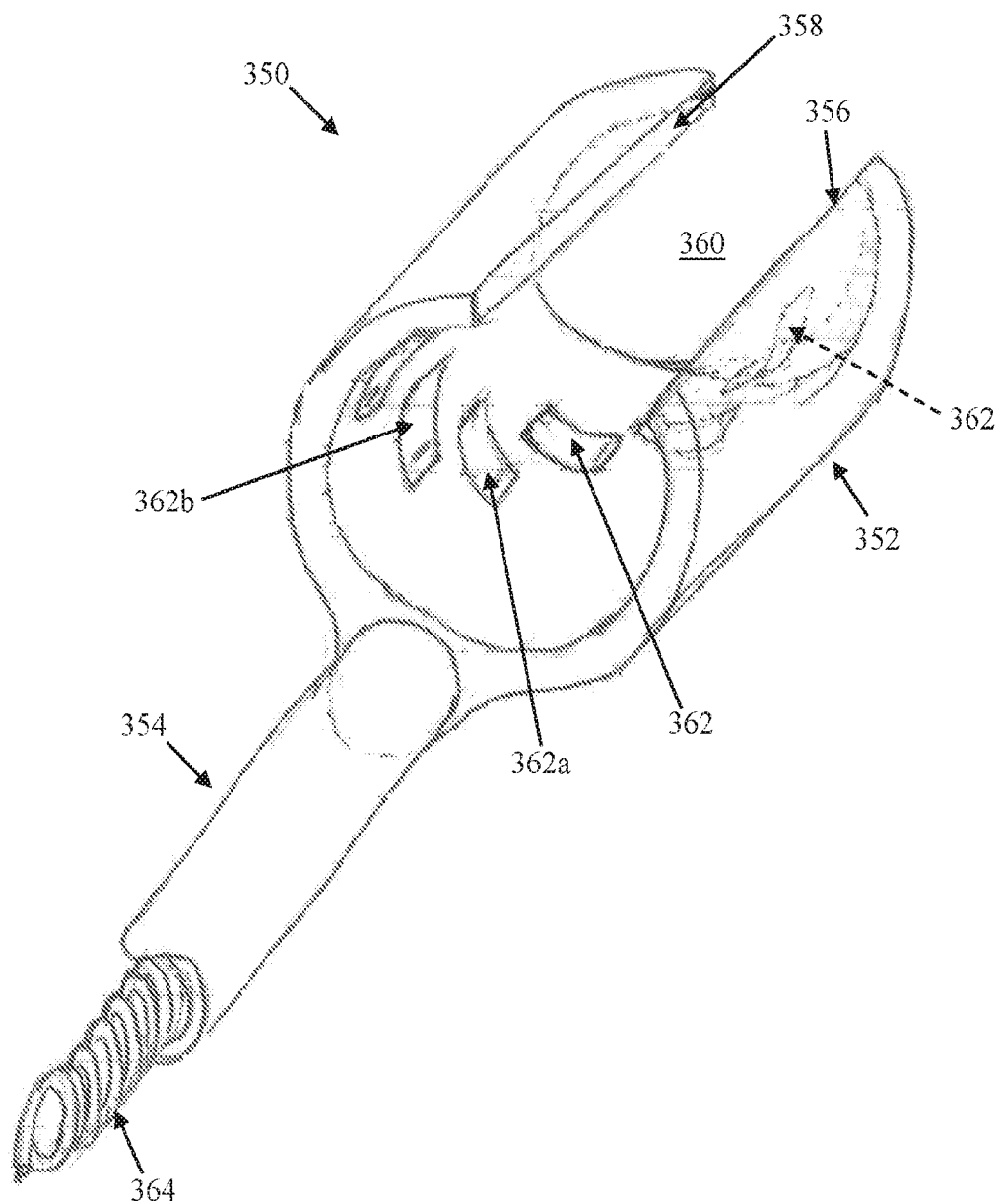
FIG. 12 is a simplified perspective view of a portion of a lead assembly useful with systems and methods of the present disclosure.

For example, a non-limiting example lead assembly 350 in accordance with principles of the present disclosure is shown in FIG. 12. The lead assembly 350 includes a cuff body 352 and a lead body 354. The cuff body 352 can be of a type or format known in the art, appropriate for placement and self-retention about or over a nerve. For example, the cuff body 352 can form or define opposing edges 356, 358, along with a central passage 360 (referenced generally). The central passage 360 can be accessed via a spacing or gap between the opposing edges 356, 358, with the cuff body 352 configured to normally or naturally self-assume or self-revert to a capture state in which the opposing edges 356, 358 are biased toward one another (it being understood that in the illustration of FIG. 12, the opposing edges 356, 358 have been slightly retracted from one another to better show other features of the lead assembly 350).

The cuff body 352 carries a plurality of stimulating elements or electrodes 362. While six of the electrodes 362 are shown in FIG. 12, any other number, either greater or lesser, is also acceptable. The electrodes 362 can be arranged in an array-like pattern along the cuff body 352. Various ones of the electrodes 362 can be longitudinally and/or circumferentially off-set from one another. For example, the electrode labeled as 362a is off-set from the electrode labeled as 362b in both a longitudinal direction (i.e., in a direction of a longitudinal axis defined by the central passage 360) and a circumferential direction (i.e., relative to a circumference of the shape defined by the cuff body 352). The array reflected by FIG. 12 is but one example of an electrode pattern envisioned by the present disclosure. Electrical connections or wiring 364 for each of the electrodes 362 is carried within the cuff body 352 in an electrically isolated fashion. As is known in the art, the electrode wiring or conductors passes from the base cuff body 352 to the lead body 354 that in turn carries the electrode wiring in an electrically isolated fashion to a proximal region (not shown) formatted for physical and electrical connection to an implantable pulse generator. The wiring or conductors 364 can have a coil format as shown, a straight or cable-like format, etc.

The lead assembly 350 can be useful, for example, in promoting stimulation of specific or selected fibers of a target nerve, for example the pudendal nerve. As a point of reference, the pudendal nerve affects or controls a number of bodily functions or activities, and it can be of value to stimulate only those fiber(s) of the pudendal nerve that will affect the desired bodily function (as opposed to stimulating all fibers of the pudendal nerve). Once implanted over the pudendal nerve, trials or testing can be performed to estimate or determine which fiber(s) each of the electrodes 362 is most likely to affect when energized. The control portion 70 (FIG. 3) can be programmed to then operate the so-identified electrodes for effecting a desired treatment regimen. For example, control portion 70 can be programmed such that the electrode(s) 362 determined to be affect larger motor axons of the pudendal nerve are energized to stimulate or activate the external urethral sphincter, whereas a more continuous stimulation pattern is used to activate smaller afferent fibers for reflex response to mitigate OAB. These and similar field steering or field strength features can be applied with the lead assembly 350, and in particular the array of electrodes 362.

Sensors

Returning to FIGS. 1-3 and as alluded to above, the IPG 64 can operate (or be prompted to operate) to prompt the delivery of, cease the delivery of, and/or modulate the delivered stimulation signal based upon, or as a function of, one or more sensed parameters of the patient via information generated by the sensor(s) 62. Alternatively or in addition, information from the sensor(s) 62 can be utilized for monitoring the patient and may or may not directly implicate operation of the IPG 64. The sensor(s) 62 can include sensors formatted for implantation into the patient or sensors intended to operate external the patient. While a single sensor 62 is shown in FIG. 3, in other embodiments, two or more of the sensors 62 can be provided, and may or may not have differing formats (or sensor components). Thus, two or more of any of the sensor arrangements of the present disclosure can be provided with the treatment system for an individual patient.

In some embodiments, the sensor(s) 62 can assume various forms appropriate for implantation into a human patient (e.g., can include or incorporate a sensor component and an anchoring mechanism or element). In some embodiments the sensor 62 generally includes a sensor component in the form of or akin to a motion-based transducer. In some embodiments, the motion-based transducer sensor component of the sensor 62 can be or include an accelerometer (e.g., a multi-axis accelerometer such as a three-axis accelerometer), a gyroscope, etc., as is known in the art. In some embodiments, the sensor 62 can include or incorporate an accelerometer, which may comprise at least some of substantially the same features and attributes as the sensors described in PCT Publication No. WO 2017/184753 to Dieken et al. and entitled "ACCELEROMETER-BASED SENSING FOR SLEEP DISORDERED BREATHING (SDB) CARE", and which is incorporated herein by reference in its entirety. In other embodiments, the sensor 62 can include a differential pressure sensor component as known in the art, a sensor appropriate for sensing EMG information as known in the art, etc. Regardless of an exact form, the sensor component of the sensor 62 is capable of sensing, amongst other things, information indicative of one or more physiological parameters of the patient described below.

A particular format of the sensor 62 can be selected as a function of the parameter(s) to be sensed, and the manner in which the IPG 64 will be controlled in response to the sensed parameter (e.g., the responsiveness or speed of IPG control). The sensor 62 can be a component separate from the stimulation element 66. In other embodiments, the stimulation element 66 can further serve as the sensor from which the parameter of interest can be determined and/or the sensor component of the sensor 62 can be carried by the lead body of the stimulation element 66.

The sensor(s) 62 can be directly connected to the IPG 64 (or the control portion 70 otherwise controlling operation of the IPG 64) via a lead body carrying or terminating at the sensor component. In other embodiments, the sensor 62 can be provide as part of a sensing unit that includes or incorporates a computer-like device (e.g., processor, memory and/or computer logic) to process information signaled from the sensor component for delivery to the control portion 70. In yet other embodiments, the sensor 62 can be carried by the IPG 64 assembly (e.g., carried within the housing of the IPG 64 assembly).

In some non-limiting examples, the sensor 62 can be a differential pressure sensor or the like configured to be implanted at a desired target site. For example, with some systems and methods of the present disclosure, the sensor 62 is or includes a differential pressure sensor or the like implanted near the bladder 10 or the urethra 14 to detect pressure increases and/or basal pressure levels of the bladder 10 or the urethra 14. In other optional embodiments, the sensor 62 is or includes a pressure sensor (e.g., a differential pressure sensor) or the like implanted near or on muscles and/or bone in a region of the pelvic floor 18 to sense information indicative of pelvic floor pressure dynamics. With these and related embodiments, the pressure sensor 62 can be placed on the hip bone or the pelvic floor 18.

In some non-limiting examples, the sensor 62 can be a motion-based transducer sensor (e.g., accelerometer such as a three axes accelerometer) configured to be implanted at a desired target site. For example, with some systems and methods of the present disclosure, the sensor 62 is or includes a motion-based transducer sensor component implanted on top of a targeted muscle layer, such as the pelvic floor muscles 18, the detrusor muscle 30, the external urethral sphincter 34, the external anal sphincter, etc.

In some non-limiting examples, the sensor 62 can be configured and located to facilitate the sensing of bioimpedance (bioelectrical impedance) information, for example detecting pelvic floor motion that is other indicative of increased pressure (or other circumstances associated with possible leakage or incontinence). As part of the bioimpedance arrangement, the sensor 62 can serve to emit or receive electrical signals appropriate for generating and collecting relevant bioimpedance information. Bioimpedance could be used to sense information indicative of one or more parameters of interest, such as bladder fullness, forces acting on the bladder indicative of a stress incontinence event or normal voiding, body motion, etc. In some embodiments, a large bioimpedance vector is beneficially provided, for example across the bladder 10 of the patient. Other muscles, tissues or organs other than the bladder 10 can also be utilized to provide bioimpedance information of interest. With this in mind, with optional embodiments in which the IPG 64 and the stimulation element 66 are implanted at opposing sides of, for example, the bladder 10, the sensor 62 can be carried within the IPG 64 assembly, with the stimulation element 66 and the sensor 62 being operated to collect bioimpedance information. In related embodiments in which the stimulation element 66 is implanted at a target site along, for example, the bladder 10, the sensor 62 can be provided as part of a sensor lead body electrically coupled to the IPG 64 assembly and arranged to locate the sensor 62 along the bladder 10 generally opposite the stimulation element 66. In yet other embodiments, a bioimpedance signal delivery element (e.g., an electrode) can be provided apart from the stimulation element 66 and that is implanted at a location generally opposite a location of the sensor 62. In yet other embodiments, the sensor 62 can be configured to be externally worn by the patient, and provided as part of a sensor unit that delivers sensed information wirelessly to the control portion 70.

In some non-limiting embodiments, the sensor 62 can be configured and located to facilitate the sensing of electromyography (EMG) information, for example indicative of motor activity that implicates urinary and/or fecal leakage (or other incontinence-related information). As part of the EMG arrangement, the sensor 62 can serve to emit or receive electrical signals appropriate for generating and collecting relevant EMG information. In some embodiments, EMG information is beneficially provided, for example, relative to the detrusor muscle 30, the external urethral sphincter 34, the external anal sphincter, the abdominal wall, or the pelvic floor muscles 18. Other muscles, tissues or organs can also serve as the target site for EMG information. In some optional embodiments, the stimulation element 66 and the sensor 62 can be implanted and operated to collect EMG information. In other embodiments, an EMG signal delivery element (e.g., an electrode) can be provided apart from the stimulation element 66 and that is implanted at a location along the target muscle generally opposite a location of the sensor 62. In yet other embodiments, a combination of abdominal wall EMG sensor and an accelerometer (or the like) sensor can be provided and acted upon as a surrogate for direct intra-abdominal pressure sensing. The accelerometer signal can generate information implicating occurrence of an acute event by the patient such as coughing, Valsalva, laughing, sneezing, etc., that would cause an increased intra-abdominal pressure without a corresponding abdominal wall contraction (e.g., the abdominal wall EMG sensor may not directly sense the acute event).

Figure 13:
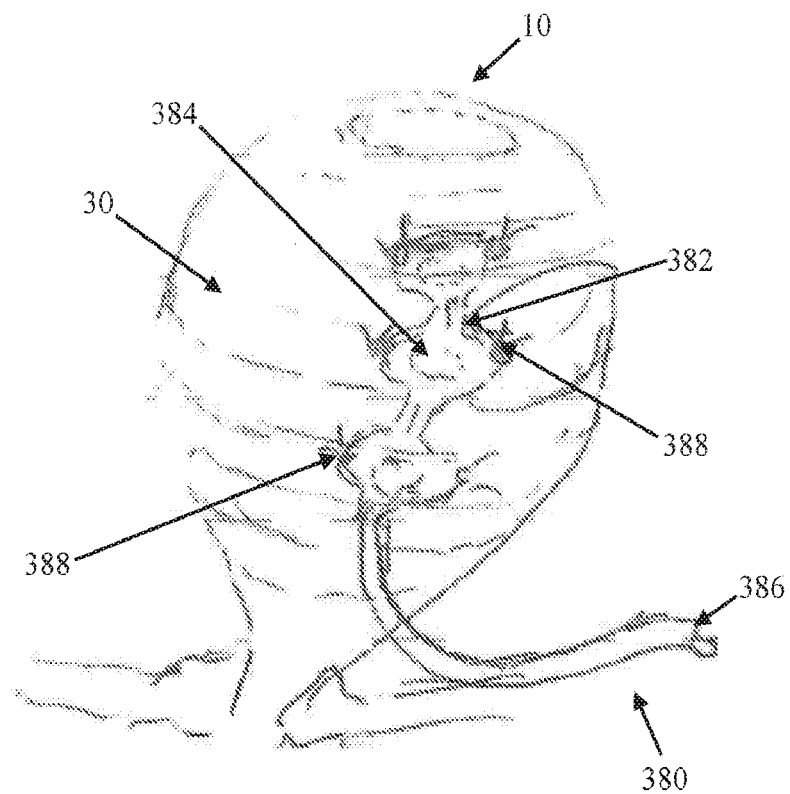
FIG. 13 is a simplified side perspective view of a sensor assembly useful with systems and methods of the present disclosure implanted to a bladder.

One non-limiting example of an EMG sensor arrangement 380 in accordance with principles of the present disclosure is provided in FIG. 13. The EMG sensor arrangement 380 includes a flexible carrier body 382 maintaining one or more electrodes 384 appropriate for sensing EMG information, and a lead body 386. The electrodes 384 can be formed with or secured to the carrier body 382 in various manners as is known in the art, with corresponding electrical connections or wiring being carried within a thickness of the carrier body 382. The carrier body 382, in turn, is formed of an electrically non-conductive material, and is sized and shaped for attachment to a target site of interest, such as an exterior of the bladder 10 (to thus obtain information relating to the detrusor muscle 30). For example, the carrier body 382 can be relatively thin and flexible, capable of adjusting to a shape and/or contour of the bladder 10. Further, a perimeter shape of the carrier body 382 can provide regions of enlarged surface area appropriate for securement to the bladder 10, for example by sutures 388 that attach the carrier body 382 to a face of the detrusor muscle 30. Regardless, the electrode wiring passes from the carrier body 382 to the lead body 386 that in turn carries the electrode wiring in an electrically isolated fashion to a proximal region (not shown) formatted for physical and electrical connection to an implantable pulse generator or similar electronic device.

Figure 14:
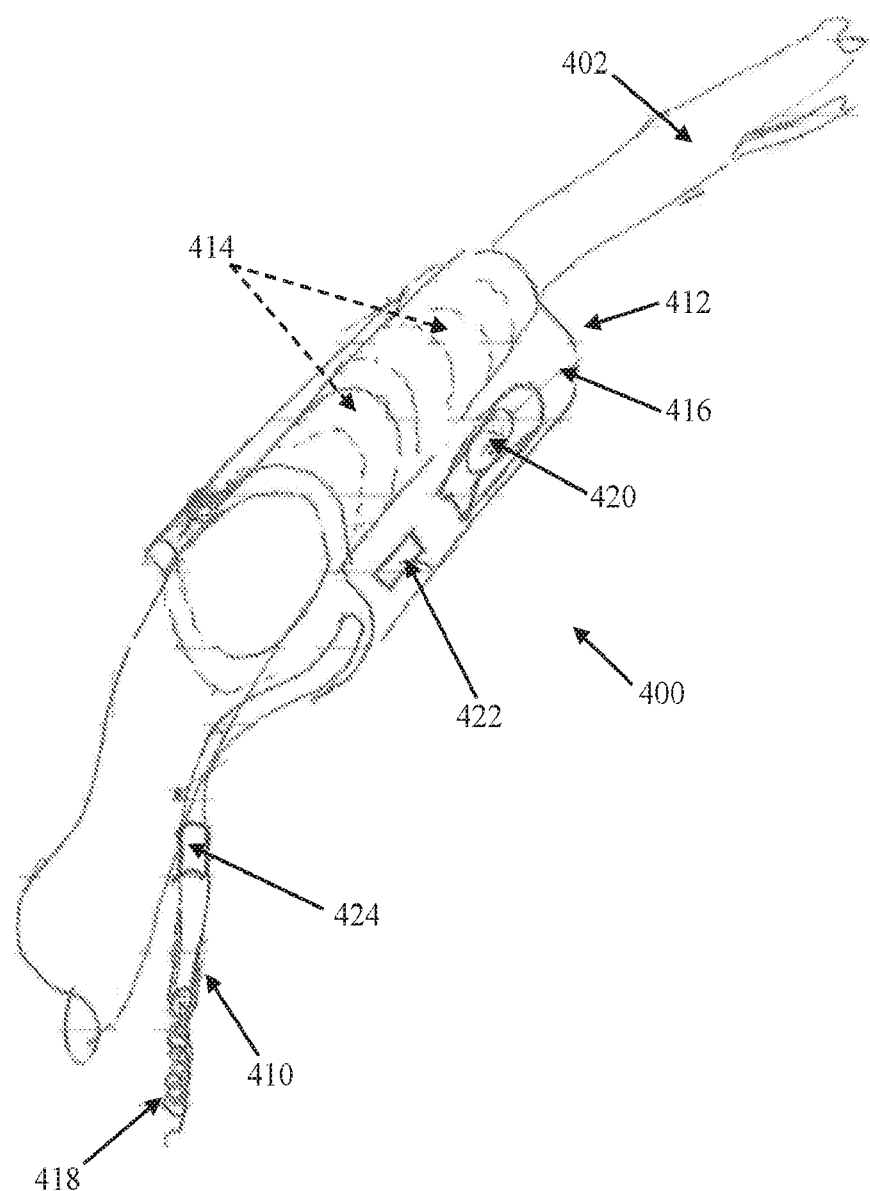
FIG. 14 is a simplified perspective view of a portion of a lead assembly useful with systems and methods of the present disclosure implanted to a nerve.

As mentioned above, in some embodiments the sensor(s) can be provided with the lead assembly otherwise carrying the stimulation element(s). For example, FIG. 14 illustrates one non-limiting example of a lead assembly 200 in accordance with principles of the present disclosure having stimulation and sensing features. As a point of reference, FIG. 14 depicts the lead assembly 400 applied to a target nerve 402 (e.g., the pudendal nerve). The lead assembly 400 includes a lead body 410 carrying or attached to a cuff body 412. The cuff body 412 can have a format conducive to atraumatic placement and retention over or about a nerve (e.g., an expandable frame) as is known in the art, and carries one or more stimulating elements or electrodes 414. The stimulating elements 414 are similarly formatted for placement and retention over or about a nerve (e.g., C-shaped or U-shaped electrodes). The cuff body 412 further forms or provides a base 416 in which electrical connections or wiring 418 for each of the stimulating elements 414 is maintained in an electrically isolated fashion. As is known in the art, the electrode wiring passes from the base 416 to the lead body 410 that in turn carries the electrode wiring in an electrically isolated fashion to a proximal region (not shown) formatted for physical and electrical connection to an implantable pulse generator.

The lead assembly 400 further includes one or more sensors each electrically connected to wiring carried by the lead body 410. For example, the lead assembly 400 can include a pressure sensor 420 attached to and carried by the cuff body base 416. The pressure sensor 420 can be of a type known in the art, and in some embodiments is or includes a pressure sensor membrane. The lead assembly 400 can further include one or more bioimpedance sensors or electrodes, for example a first bioimpedance sensor 422 attached to and carried by the base 416, and a second bioimpedance sensor 424 attached to and carried by the lead body 410. A location of a bioimpedance sensor along the lead body 410 (e.g., the second bioimpedance sensor 424) can be selected in accordance with a targeted anatomy upon final implant of the cuff body 412. Alternatively or in addition, one or both of the bioimpedance sensors 422, 424 can be used to sense muscle activity (EMG); the features could be applied to any of the cuff and/or lead assembly constructions of the present disclosure. With these and related embodiments, EMG measurements could be made along a vector from the lead to the pulse generator. In some non-limiting examples, the lead assembly 400 is configured to locate the stimulating elements 414 along the pudendal nerve near the pelvic floor.

Returning to FIGS. 1-3, in some non-limiting embodiments, the sensor 62 can be configured and located to facilitate the sensing of information external the patient. For example, the sensor 62 can be or can be akin to a moisture sensor that is provided as part of a sensor unit configured to be worn by the patient (e.g., a pad) at a location where the sensor 62 detects a leakage event. Other externally-worn sensor arrangements are also envisioned. In some embodiments, information from the external sensor can be communicated to (e.g., via wireless connection), and optionally acted upon, the IMD 60 as described elsewhere in the present disclosure (e.g., where the external sensor 62 is a moisture sensor and senses information indicative of a leakage event, the IMD 60 can be operated (e.g., via a programmed feedback loop) to initiate delivery of stimulation therapy formatted to limit the leakage event from continuing). Additionally or alternatively, information from the external sensor (or any other of the sensor arrangements of the present disclosure) can be communicated to one or both of the patient and caregiver as described below. As a point of reference, knowledge of a leakage event can be useful to a patient, for example, who might not otherwise realize the event is occurring, and/or can be useful to a caregiver in monitoring efficacy of various treatment protocols.

In yet other embodiments, the sensor(s) 62 can be configured and located to sense information indicative of filling or a volume and/or a pressure of the patient's bladder 10 and/or of the patient's rectum 12 (or colon). By way of non-limiting example, information indicate of volume can be obtained by ultrasound, impedance, etc., that is calibrated for the particular patient; similarly, information indicative or pressure can be obtained by a pressure-type sensor located on a waistband of the patient's clothing. Regardless, with these and related embodiments, the IMD 60 can be programmed to operate in response to sensed volume and/or pressure information. For example, where a determination is made that the volume and internal pressure of the patient's bladder (or rectum/colon) is high, it can be assume that the patient is ready to void the treatment system can be operated so as to encourage voiding (e.g., end stimulation signals intended to relax the detrusor muscle, alert the patient of a need to void, etc.). In yet other embodiments in which a sensor is provided that senses information indicative of the patient's bladder being full, the IMD 60 can be operated, for example, to stimulate baroreceptors of the bladder that in turn signal the patient's brain that the bladder is full (or other afferent stimulation).

Stimulation Methods and Algorithms

Regardless of how the patient-related information is sensed and delivered, some methods of the present disclosure can include prompting the IMD 60 to initiate delivery of, cease delivery of and/or modulate one or more of the stimulation signals (e.g., via programming provided with the control portion 70) based upon or as a function of the sensed patient-related information. In some examples, the stimulation signal is initiated and/or modulated based on sensed patient information. In some examples, one or more of the amplitude, rate, and pulse duration of the stimulation signal is modulated based upon, for example, the sensed patient information. Alternatively or in addition, the duty cycle of the stimulation signal is altered in response to the sensed patient information.

With some example systems and methods of the present disclosure, the stimulation element 66 is located to deliver electrical stimulation sufficient to activate the external urethral sphincter 34 for treatment of urinary incontinence. For example, and as identified in FIG. 2, the stimulation element 66 can be implanted so as to deliver electrical stimulation directly to the external urethral sphincter 34 (designated as location 80 in FIG. 2), with the control portion 70 programmed to prompt the IPG 64 to generate a stimulation signal with parameters (e.g., intensity, frequency, duty cycle, etc.) appropriate to cause the external urethral sphincter 34 to activate or contract. In other embodiments, the stimulation element 66 can be implanted so as to deliver electrical stimulation to the pudendal nerve 44 or an appropriate branch thereof (two possible locations are identified at 82 and 84 in FIG. 2), with the control portion 70 programmed to prompt the IPG 64 to generate a stimulation signal with parameters (e.g., intensity, frequency, duty cycle, etc.) appropriate to cause the external urethral sphincter 34 to activate or contract in response to the pudendal nerve 44. Similar arrangement and configurations are alternatively employed relative to the external anal sphincter for treatment of fecal incontinence. With some embodiments in which the stimulation element 66 is located to stimulate the pudendal nerve 44 (or other nerves) to effect contraction or closure of the external urethral sphincter 34 (or external anal sphincter) for the treatment of stress incontinence, the systems and methods of the present disclosure can be selected to target or stimulate the efferent neurons (as opposed to the afferent neurons). As such, in some embodiments, the systems and methods of the present disclosure can include delivering high frequency stimulation energy, for example on the order of 30 Hz or greater. In other embodiments, the delivered stimulation energy can have a frequency of less than 30 Hz. In yet other embodiments, the delivered stimulation energy can be formatted stimulate afferent neurons.

With some example systems and methods of the present disclosure, the control portion 70 is programmed to prompt the provision of appropriate stimulation energy to the targeted nerve and/or muscle on a fully dynamic basis. For example, the control portion 70 can be programmed to initiate the delivery of stimulation energy upon determining the occurrence of a patient event or circumstance (via information from the sensor 62) indicative of potential leakage (urine leakage or fecal leakage). The control portion 70 can be further programmed to continue the delivery of the stimulation energy for a predetermined length of time and/or until the determined patient event or circumstance has subsided or ended. For example, the control portion 70 can include or be programmed to include or provide a monitoring engine and a therapy engine. The monitoring engine is programmed to evaluate information from the sensor(s) 62 (along with, in some embodiments, information from other sources such as other sensors associated with the patient) to determine or designate the likelihood of a possible leakage event or circumstances (e.g., expansion of the bladder 10). Once the monitoring engine has determined the existence of potential leakage, the therapy engine is prompted to initiate the delivery of stimulation energy with predetermined parameters deemed appropriate to suppress leakage from occurring (e.g., sufficient to activate the external urethral sphincter 34).

With some example systems and methods of the present disclosure, the control portion 70 is programmed to prompt the provision of appropriate stimulation energy to the targeted nerve and/or muscle (including selectively providing simulation to two or three or more target sites) on a dynamic basis and on a basal basis. For example, the control portion 70 can be programmed to provide a basal level of stimulation to help prevent leakage in addition to the dynamic protection against leakage as described above. In some embodiments, the basal stimulation can be modulated to minimize undesired stressing or fatiguing of the muscle(s) being stimulated. For example, the control portion 70 can include or be programmed to include a therapy engine that provides a dynamic mode of operation as described above, and a basal mode of operation. The basal mode can be programmed to modulate the delivered stimulation energy by way of a predetermined on/off duty cycle, ramping up/down the delivered stimulation energy in a predetermined manner, etc. In yet other optional embodiments, the systems and methods of the present disclosure can be configured and programmed to deliver stimulation energy to two (or more) target sites. With these and related embodiments, the basal mode of operation can include rotating between the target site receiving stimulation energy. In yet other embodiments, the basal mode of operation can include increasing the level of delivered stimulation in response to the detection of increasing pressure at one or more locations of the patient (e.g., via information from the sensor 62), such as one or more of the bladder 10, the urethra 14, the pelvic floor 18, the rectum 12, etc. With these and similar embodiments, the basal mode of operation can further include providing a low level or no stimulation energy when the detected pressure is low, and then incrementally increasing the delivered stimulation energy as the detected pressure increases (e.g., akin to functioning of a healthy external urethral sphincter 34). In yet other embodiments, low level stimulation energy (e.g., tonal level) is applied to increase sphincter tone, and dynamic stimulation (or dynamic stimulation mode) with a stimulation higher than or ramped up from the tonal level as described above can be effected when desired or deemed appropriate; with these and related embodiments, the dynamic stimulation would be additive to the tonal level, thereby minimizing the time response to a maximal sphincter contraction. The tonal level or low level stimulation energy can be applied on a constant or continuous basis, or can be applied over intervals of time (e.g., a repeating cycle of 30 seconds on, 10 seconds off) independent of the signals prompting delivery of dynamic or additive stimulation energy.

With some example systems and methods of the present disclosure, the control portion 70 is programmed to prompt the provision of appropriate stimulation energy to the targeted nerve and/or muscle on only the basal basis as described above (e.g., without dynamic support).

With some example systems and methods of the present disclosure, the control portion 70 is programmed to prompt the provision of appropriate stimulation energy to the targeted nerve and/or muscle to treat mixed incontinence. With these and related embodiments, the control portion 70 can be configured or programmed to provide one or both of the dynamic and basal modes of operation as described above to reduce or treat stress incontinence. Further, the control portion 70 can be configured or programmed to prompt the stimulation of a target site(s) appropriate to cause the detrusor muscle 30 to relax (thus preventing or reducing urge incontinence or frequency) in an urge mode of operation. For example, stimulation energy can be applied to stimulate the pelvic floor nerves (sacral, pudendal 44) at levels that cause the detrusor muscle 30 to relax. With these and related embodiments, the therapy engine provided with or programmed to the control portion 70 can include a urge incontinence mode that is programmed to prompt an increase in the delivered stimulation energy (e.g., duty cycle or other stimulation energy parameters) as the bladder 10 is determined to be filling to better ensure appropriate detrusor relaxation.

In optional, related embodiments, the control portion 70 can be programmed to effectuate a progressive recruitment therapy routine. For example, the control portion 70 can be programmed such that upon determining or estimating an initial need to provide incontinence therapy (e.g., onset of a leakage or potential leakage event; sensed pressure at the bladder 10; etc.) to prompt application of stimulation energy to activate the external urethral sphincter 34; as the need for incontinence therapy is determined to have increased over time (e.g., pressure at the bladder 10 is determined to have increased by a predetermined amount over a predetermined period of time and/or exceeds a predetermined threshold), the control portion 70 is programmed to prompt application of additional stimulation energy, for example to further recruit activation of the pelvic floor muscles 18, increased intensity of stimulation energy that activates the external urethral sphincter 34, etc.

The control portion 70 can be programmed to learn over time of circumstances where leakage (or other incontinence event) is likely to occur for the patient, for example by correlating an indicated leakage event from the patient with various sensor information at the time of the leakage event (e.g., information from an activity sensor (e.g., accelerometer), abdominal pressure sensor, bladder volume sensor, EMG sensor(s), etc.). The learned information can then be applied by the control portion 70 for future stimulation therapy, automatically adjusting or increasing stimulation when sensor information indicates that a leakage event is likely to occur, and at other times avoiding the delivery of unwanted stimulation amplitudes, durations and/or frequency that might otherwise be uncomfortable for the patient.

Figure 15A:
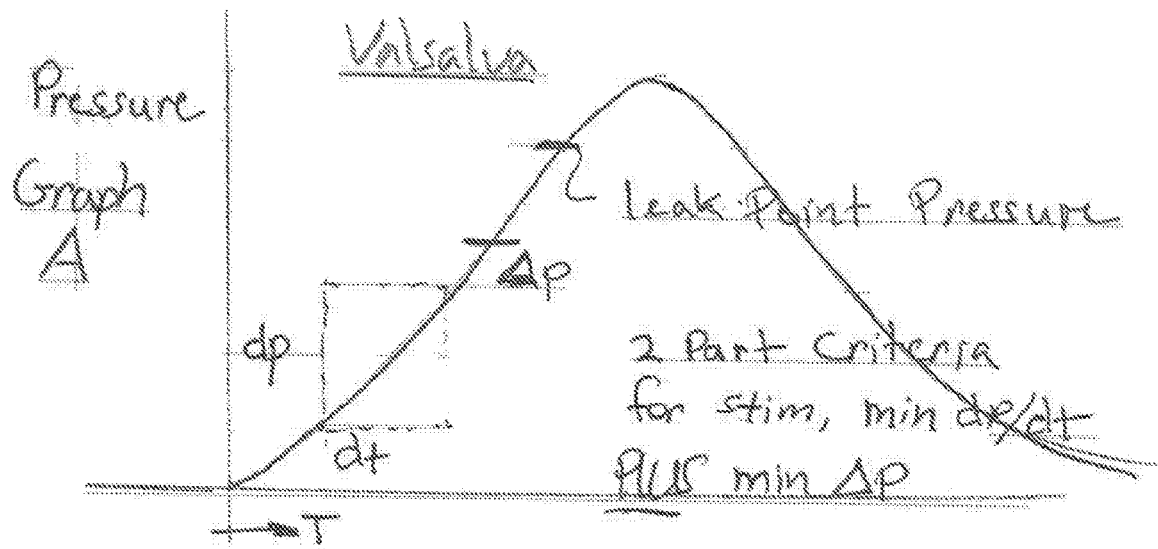
FIGS. 15A and 15B are graphs illustrating algorithms useful with systems and methods of the present disclosure for estimating a potential leakage event.
Figure 15B:
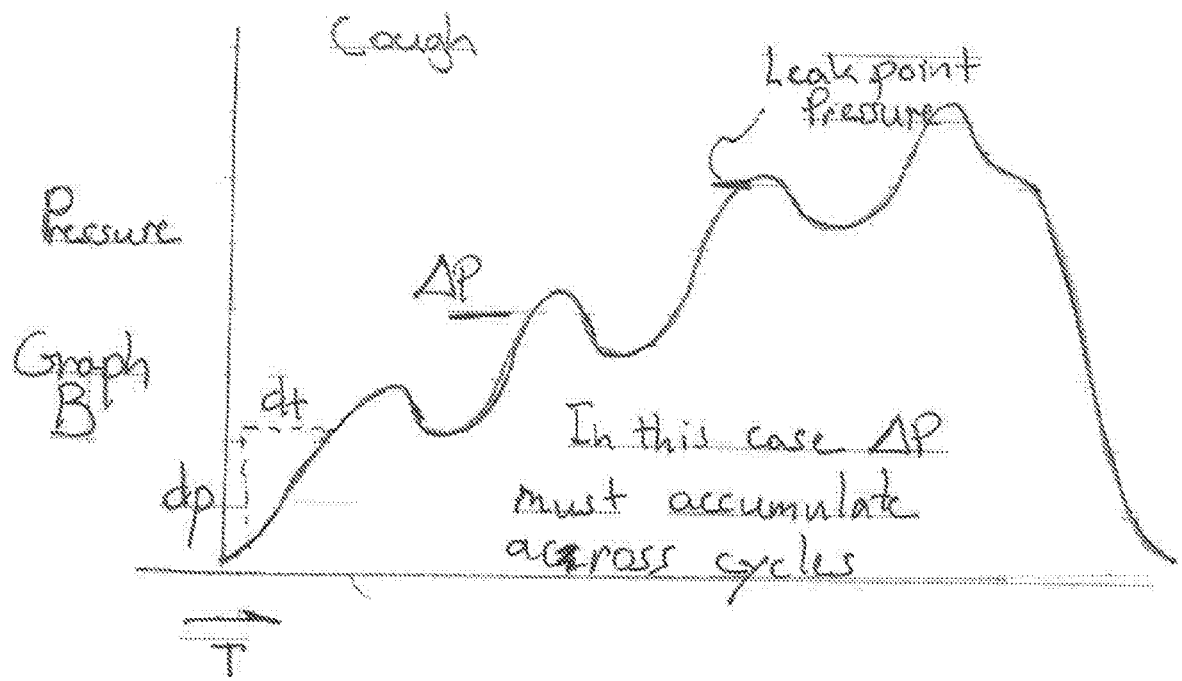

Some non-limiting examples of algorithms useful for predicting occurrence of a possible leakage event based on sensor information are provided in FIGS. 15A and 15B. With this non-limiting embodiment, sensed abdominal pressure can be utilized to predict possible occurrence of a leak event, and action taken (e.g., increased stimulation) prior to the predicted leak event. In the graph of FIG. 15A, abdominal pressure over time is plotted, and a pressure at which a leak event has been determined to likely occur is noted. Where the sensed pressure or change pressure in a single sensing cycle (noted a "□p" in FIG. 15A) and the change in pressure over time (dp/dt) is greater than a predetermined or threshold value, stimulation treatment can be initiated or increased. Alternatively or in addition, with the algorithm implicated by the plot of FIG. 15B, initiation or increase in stimulation treatment occurs when the sensed change in pressure threshold is determined to have occurred over a predetermined number of sensing cycles (thereby accounting for occurrence of a temporary increase in abdominal pressure that might not directly implicate an expected leak event based on a pressure, such as when the patient coughs).

Returning to FIGS. 1-3, the stimulation therapy algorithms or protocols of the present disclosure (as implemented, for example, by the control portion 70) can, in some non-limiting examples, provide for dynamic stimulation level adjustment or modulation based, for example, on information from the sensor(s) 62 under one or more scenarios. In some embodiments, the control portion 70 is programmed to increase stimulation delivered to the patient in response to an elevated change in a sensed or monitored parameter of the patient, for example intra-abdominal pressure (e.g., the sensor 62 is sensing a property of the patient that indicates abdominal pressure or intra-abdominal pressure, and the control portion 70 determines and monitors the change in the pressure over time (dp/dt)). If, for example, the determined dp/dt is high (e.g., exceeds a predetermined threshold value), stimulation intensity is automatically increased (proportionally, in a step level, or some other relationship). This could address, for example, more severe events experienced by the patient, such as a more aggressive cough with higher level muscle contraction. The elevated stimulation intensity might be uncomfortable, but can be selected to be acceptable to the patient.

In some embodiments, the control portion 70 is programmed to increase stimulation delivered to the patient in response to an elevated change in a sensed or monitored parameter of the patient, for example intra-abdominal pressure (e.g., the sensor 62 is sensing a property of the patient that indicates abdominal pressure or intra-abdominal pressure, and the control portion 70 determines and monitors the change in the pressure over time (dp/dt)). If, for example, monitored pressure is high but not at a level implicating the delivery of stimulation (e.g., a current pressure does not exceed a predetermined threshold) and a subsequent rapid or faster increase in dp/dt (e.g., dp/dt exceeds a predetermined threshold value) to a pressure level that does implicate the delivery of stimulation, the stimulation intensity prompted by the control portion 70 would be higher than a normal or nominal intensity.

In some embodiments, the control portion 70 is programmed to increase stimulation delivered to the patient in response to an elevated change in a sensed or monitored pressure parameter (dp/dt) of the patient as a function of sensed volume (e.g., bladder volume). If, for example, the monitored change in pressure (dp/dt) implicates the delivery of stimulation and the monitored volume is high (e.g., exceeds a threshold value), the stimulation intensity prompted by the control portion would be higher than a normal or nominal intensity.

In some embodiments, the control portion 70 is programmed to decrease or suppress stimulation as a function of sensed volume (e.g., bladder volume). For example, the control portion 70 can be programmed to suppress or not deliver stimulation if the monitored volume is below a threshold value. Alternatively or in addition, the control portion 70 can be programmed to suppress or not deliver stimulation if the monitored volume is deemed to be low (e.g., below a threshold) unless the monitored pressure (e.g., intra-abdominal pressure) and/or change in a sensed or monitored pressure parameter (dp/dt) of the patient is high (e.g., exceeds a threshold).

In some embodiments, the control portion 70 is programmed to provide an increased stimulation intensity (as compared to a normal or nominal stimulation intensity being delivered to the patient, or to be delivered under a dynamic mode of operation) as a function of a body position of the patient. For example, the control portion 70 can be in communication with a sensor(s) providing information indicative of the patient's body position (e.g., an accelerometer). Where the body position information indicates that the patient is standing, for example, the control portion 70 is programmed to prompt delivery of an increased stimulation intensity. Alternatively or in addition, in some embodiments the control portion 70 is programmed to implement an increased sensitivity factor responsive to dp/dt based upon a sensed body position of the patient. For example, where the body position information indicates that the patient is prone or flexing at the torso (and thus naturally causing an increase in the patient's intra-abdominal pressure), the control portion 70 can be programmed to increase a sensitivity to dp/dt information and/or to increase delivered stimulation intensity above the normal or nominal dynamic level.

In some embodiments, the control portion 70 is programmed to provide an increased stimulation intensity (as compared to a normal or nominal stimulation intensity being delivered to the patient, or to be delivered under a dynamic mode of operation) as a function of sensed movement of the patient. Where the body movement information indicates that the patient is running or jumping, for example, the control portion 70 is programmed to prompt delivery of an increased stimulation intensity.

In some embodiments, the control portion 70 is programmed such that a sensitivity factor (or likelihood of delivering stimulation) implemented by the control portion 70 in determining whether or not to prompt delivery of stimulation can be adjusted by the patient. For example, the patient can decrease the stimulation factor (and thus decrease the likelihood of stimulation being delivered) when more comfort is desired and the patient less concerned with a possible minor leak event (e.g., the patient is at home). Conversely, the patient can increase the stimulation factor (and thus increase the likelihood of stimulation being delivered) when in a situation where a possible leak event is less acceptable (e.g., the patient is at a gym or other public setting) and more stimulation sensation is an acceptable tradeoff.

Figure 16A:
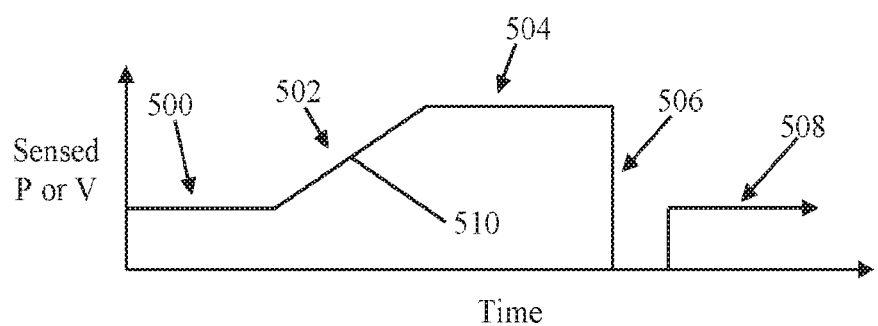
FIGS. 16A-16E are graphs illustrating algorithms useful with systems and methods of the present disclosure for applying stimulation energy in the treatment of incontinence.

Non-limiting examples of possible stimulation protocols or modulations implemented by the systems and methods of the present disclosure in accordance with the descriptions and algorithms above are provided in FIGS. 16A-16E. The plot of FIG. 16A represents a monitored or sensed physical parameter of the patient relating to continence, for example pressure P (e.g., bladder pressure, abdominal pressure, etc.), volume V (e.g., bladder volume), etc., over time. The monitored parameter is relatively constant over a baseline or normal period 500, gradually increases over an increasing period 502 (e.g., indicative of increased urine in the bladder) until reaching a heighted level where the monitored parameter remains relatively constant over a heightened period 504, and then drops to zero or near zero at 506 (e.g., indicative of the patient voiding). The monitored parameter later rises to the normal level at 508. In some embodiments of the present disclosure, sensed information implicating the monitored parameter or trace of FIG. 16A is provided to or acted upon the control portion 70 (FIG. 3). In related embodiments, the control portion 70 can be programmed to designate or respond to a threshold value or level in the monitored parameter. For example, one possible threshold 510 is identified in FIG. 16A that is attained or occurs along the increasing period 502; the threshold 510 could represent an absolute value of the monitored parameter, the change in the monitored parameter over time, etc.

Figure 16B:
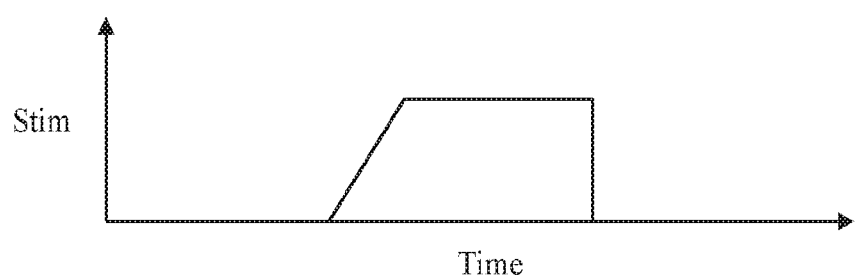

FIG. 16B represents one stimulation protocol or algorithm implemented by some embodiments of the present disclosure responsive to the monitored parameter of FIG. 16A. With the approach of FIG. 16B, stimulation ("Stim") is initiated when the threshold 510 is reached (e.g., when the monitored parameter is at the normal level (or otherwise below the threshold 510), no stimulation energy is delivered to the patient). Once the monitored parameter reaches the threshold 510, stimulation energy begins and gradually increases (e.g., intensity, pulse width, frequency, etc.), optionally in a predetermined manner. The delivered stimulation continues to increase until the monitored parameter is identified as having transitioned to the heighted period 504 (i.e., the monitored parameter can be viewed as being elevated, but no longer increasing); at this point, the stimulation energy continues to be delivered to the patient, but at a more constant level. Finally, when the monitored parameter drops below the threshold (e.g., the drop at 506), stimulation energy is stopped or no longer delivered to the patient.

Figure 16C:
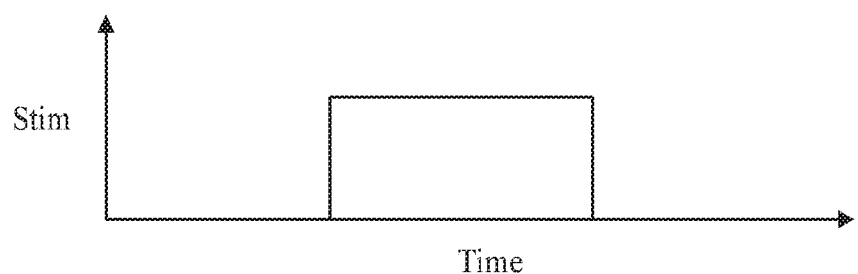

FIG. 16C represents another stimulation protocol or algorithm implemented by some embodiments of the present disclosure responsive to the monitored parameter of FIG. 16A. With the approach of FIG. 16C, stimulation ("Stim") is initiated when the threshold 510 is reached (e.g., when the monitored parameter is at the normal level (or otherwise below the threshold 510), no stimulation energy is delivered to the patient). Once the monitored parameter reaches the threshold 510, stimulation energy is delivered at a set intensity level and remains at this set level until the monitored parameter drops below the threshold (e.g., the drop at 506). At this point, stimulation energy is stopped or no longer delivered to the patient.

Figure 16D:
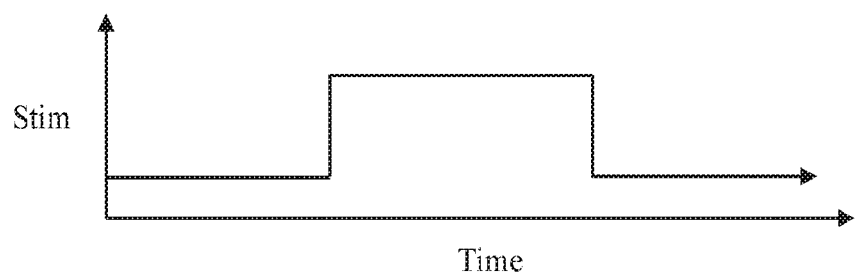

FIG. 16D represents another stimulation protocol or algorithm implemented by some embodiments of the present disclosure responsive to the monitored parameter of FIG. 16A. With the approach of FIG. 16D, basal or low level stimulation ("Stim") is continuously delivered to the patient regardless of whether the monitored parameter has reached or attained the threshold 510, and thus occurs during the normal period 500. Once the monitored parameter reaches the threshold 510, an intensity of the stimulation energy being delivered is increased to a second level and remains at this second level until the monitored parameter drops below the threshold (e.g., the drop at 506). At this point, the stimulation energy intensity is reduced to the basal or low level.

Figure 16E:
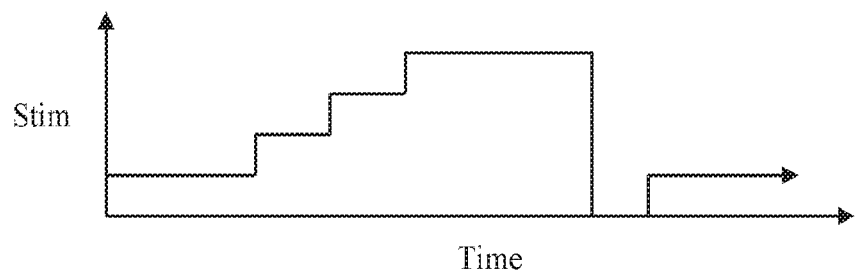

FIG. 16E represents another stimulation protocol or algorithm implemented by some embodiments of the present disclosure responsive to the monitored parameter of FIG. 16A. With the approach of FIG. 16E, basal or low level stimulation ("Stim") is continuously delivered to the patient regardless of whether the monitored parameter has reached or attained the threshold 510, and thus occurs during the normal period 500. Once the monitored parameter is identified as increasing (i.e., initiation of the increasing period 502), an intensity of the stimulation energy being delivered is increased. The increase in stimulation energy intensity is formatted to occur in a stepwise fashion as implicated by FIG. 16E. So long as the monitored parameter is identified as increasing or at least not decreasing faster than a specific rate or dropping below an established value, an intensity of the stimulation energy being delivered to the patient is periodically increased. The delivered stimulation continues to increase in a step-like manner until the monitored parameter is identified as having transitioned to the heighted period 504 (i.e., the monitored parameter can be viewed as being elevated, but no longer increasing); at this point, the stimulation energy continues to be delivered to the patient, but at a more constant level. Finally, when the monitored parameter drops in a rapid manner (e.g., the drop at 506), stimulation energy is stopped or no longer delivered to the patient. The basal or low level stimulation is reinitiated once the monitored parameter is deemed as being at the normal level (i.e., 508 in FIG. 16A).

Non-limiting examples of possible stimulation patterns or protocols implemented by the systems and methods of the present disclosure in accordance with the descriptions and algorithms above are provided in FIGS. 17A-17C. The plot of FIG. 17A represents a monitored or sensed physical parameter of the patient relating to continence, for example pressure (e.g., bladder pressure, abdominal pressure, etc.), volume (e.g., bladder volume), etc., over time. The monitored parameter is shown to exhibit a first increasing period 530 and a second increasing period 532. An instantaneous change in the monitored parameter over time (e.g., instantaneous change in intra-abdominal pressure over time or dp/dt) can be determined by a slope of the plot line, and is indicated at 534 for the first increasing period 530, and at 536 for the second increasing period 532. The plot of FIG. 17B reflects the instantaneous change in the monitored parameter (e.g., dp/dt) over time.

FIG. 17C represents one stimulation protocol or algorithm implemented by some embodiments of the present disclosure responsive to the monitored parameter of FIGS. 17A and 17B. With the approach of FIG. 17C, stimulation level ("Stim") is increased (e.g., voltage, current, pulse width, frequency, etc.) when the instantaneous change in the monitored parameter (e.g., dp/dt) is high (e.g., exceeds a predetermined threshold), and continues at the increased level until the instantaneous change is reduced (e.g., falls below a predetermined threshold). The increase in stimulation could be increased proportionally, in a step level, or some other relationship. For example, the instantaneous change in the monitored parameter associated with the first increasing period 530 results in a first stimulation level 540, whereas the higher instantaneous change in the monitored parameter associated with the second increasing period 532 results in a second, higher stimulation level 542. These optional embodiments could address more severe events experienced by the patient, such as a more aggressive cough with higher level muscle contraction.

Non-limiting examples of possible stimulation patterns or protocols implemented by the systems and methods of the present disclosure in accordance with the descriptions and algorithms above are provided in FIGS. 18A-18C. The plot of FIG. 18A represents a monitored or sensed physical parameter of the patient relating to continence, for example pressure (e.g., bladder pressure, abdominal pressure, etc.), volume (e.g., bladder volume), etc., over time. The monitored parameter is shown to be relatively steady over a first period 550 and then experiences an increase 552 followed by a decrease 554. The plot of FIG. 18B reflects the instantaneous change in the monitored parameter (e.g., dp/dt) over time as described above.

FIG. 18C represents one stimulation protocol or algorithm implemented by some embodiments of the present disclosure responsive to the monitored parameter of FIGS. 18A and 18B. With the approach of FIG. 18C, stimulation level ("Stim") is increased (e.g., voltage, current, pulse width, frequency, etc.) when the instantaneous change in the monitored parameter (e.g., dp/dt) increases (e.g., at 552 of FIG. 18A), stimulation delivery, or higher level of stimulation than normal, is triggered at 556 (e.g., dp/dt exceeds a threshold value). Thus, for example, if pressure (or other monitored parameter) is high but not enough to trigger stimulation, then a subsequent detection of an instantaneous increase in a monitored parameter (e.g., dp/dt) would result in delivery of stimulation, where this same level of instantaneous increase would not result in delivery of stimulation if the pressure (or other monitored parameter) were below an established value. Similar, fast increase (e.g., greater dp/dt) with an elevated pressure (or other monitored parameter) would trigger a stimulation output of a higher level than normal.

Non-limiting examples of possible stimulation patterns or protocols implemented by the systems and methods of the present disclosure in accordance with the descriptions and algorithms above are provided in FIGS. 19A-19C. The plot of FIG. 19A represents a monitored or sensed pressure of the patient (e.g., bladder pressure, abdominal pressure, etc.). By way of reference, the plot of FIG. 19A is the same as FIG. 17A; thus, an instantaneous change in pressure (dp/dt) implicated by the graph of FIG. 19A is the same as the instantaneous change in pressure (dp/dt) reflected by FIG. 17B. The plot of FIG. 19B represents a monitored or sensed volume (e.g., bladder volume) of the patient over time, contemporaneous with the monitored pressure. The monitored volume is shown as gradually increasing to and beyond a threshold level 560.

FIG. 19C represents one stimulation protocol or algorithm implemented by some embodiments of the present disclosure responsive to the monitored parameters of FIGS. 19A and 19B. With the approach of FIG. 19C, stimulation level ("Stim") can be delivered at a normal level in response to, for example, the instantaneous change in the monitored pressure (e.g., dp/dt) exceeding a predetermined threshold as indicated, for example, at 562. Under circumstances where the instantaneous change in pressure implicates the delivery of stimulation and the monitored volume is high (e.g., exceeds the threshold 560), then the stimulation level or intensity (e.g. voltage, current, pulse width, frequency, etc.)

delivered to the patient is increased as compared to the normal level (as at 564). Thus, for example, if bladder volume is high, then stimulation levels would be higher for a level of dp/dt as compared to normal bladder levels.

Non-limiting examples of possible stimulation patterns or protocols implemented by the systems and methods of the present disclosure in accordance with the descriptions and algorithms above are provided in FIGS. 20A-20C. The plot of FIG. 20A represents a monitored or sensed pressure of the patient (e.g., bladder pressure, abdominal pressure, etc.). By way of reference, the plot of FIG. 20A is the same as FIG. 17A; thus, an instantaneous change in pressure (dp/dt) implicated by the graph of FIG. 20A is the same as the instantaneous change in pressure (dp/dt) reflected by FIG. 17B. The plot of FIG. 20B represents monitored or sensed activity of the patient over time, contemporaneous with the monitored pressure. The monitored activity can, for example, be generated or implicated by an accelerometer or the like as an acceleration level, mean or RMS (e.g., the jagged line 570 in FIG. 20B represents an actual acceleration signal generated by individual actions such as jumping, running, etc.; the solid line 572 in FIG. 20B represents a running average or RMS value of the acceleration that can be utilized for the algorithm to use to decide if activity levels will increase stimulation). The monitored activity level is shown as exhibiting an elevated period 574.

FIG. 20C represents one stimulation protocol or algorithm implemented by some embodiments of the present disclosure responsive to the monitored parameters of FIGS. 20A and 20B. With the approach of FIG. 20C, stimulation level ("Stim") can be delivered at a normal level in response to, for example, the instantaneous change in the monitored pressure (e.g., dp/dt) exceeding a predetermined threshold as indicated, for example, at 576. Under circumstances where the instantaneous change in pressure implicates the delivery of stimulation and the monitored activity is high (e.g., exceeds a threshold as in the elevated period 574), then the stimulation level or intensity (e.g. voltage, current, pulse width, frequency, etc.) delivered to the patient is increased as compared to the normal level (as at 578). Thus, for example, dynamic stimulation levels can be increased over nominal if the patient's body movement is unfavorable, such as running or jumping.

Returning to FIGS. 1-3, with some embodiments of the present disclosure, the control portion 70 is programmed to reduce or end the delivery of stimulation energy otherwise being applied to activate the external urethral sphincter 34 and/or the external anal sphincter or other muscle for treating stress incontinence (e.g., in one or both of the dynamic and basal modes described above) when the patient desires to void (e.g., where the system is operating to activate the external urethral sphincter 34 to prevent urinary leakage, the delivered stimulation energy can be reduced or ended to permit the external urethral sphincter 34 to relax allowing the patient to more easily void the bladder when desired). With this in mind, in some example systems and methods of the present disclosure, a remote control (e.g., the external device 68) is provided to the patient, allowing the patient to indicate that voiding is desired as described below, with the control portion 70, in turn, being programmed to reduce or end the delivery of stimulation energy. In other embodiments, the systems and methods of the present disclosure can provide at least partial control over therapy such as when a remote control is not available. Such partial control can include at least pausing therapy, starting therapy, stopping therapy and the like. With this in mind, in some examples, the control portion 70 can include or is programmed to include an activation engine that operates in response to information sensed by the sensor 62. For example, with some non-limiting embodiments in which the sensor 62 is or includes an accelerometer, the activation engine can be programmed to operate in response to the patient (or a caregiver) tapping on the patient's body in a region of the implanted sensor 62 a certain number of times within a configurable time period (e.g., three strong taps within two seconds). In some examples, this physical control may act as an alternative therapy deactivation mechanism, such as when the IPG 64 is accidentally activated and/or when the patient desires to void.

In related embodiments, the control portion 70 is programmed to provide (or not provide) stimulation energy at selected levels in response to other volition control scenarios. For example, the control portion 70 can be programmed to operate in an exercise mode upon prompting by the patient or a caregiver (e.g., via the external device 68). The exercise mode can include the provision of stimulation energy to targeted nerve(s) and/or muscle(s) while the patient engages in certain exercises intended improve incontinence (e.g., Kegel exercises).

In yet other embodiments, the control portion 70 is programmed to reduce or end the delivery of stimulation energy otherwise being applied to activate the external urethral sphincter 34 and/or the external anal sphincter or other muscle for treating stress incontinence (e.g., in one or both of the dynamic and basal modes described above) upon self-determining that the patient desires to void. The determination of desired voiding can be based upon information from the sensor 62 and/or other sensors providing information that indicates a desire to void (e.g., a voluntary or involuntary attempt to relax one or more of the sphincters 32, 34, contract the detrusor muscle 30, etc.). With these and related embodiments, the control portion 70 can be programmed to distinguish between a desired void event and a stress event (e.g., the delivery of stimulation energy to activate the external urethral sphincter is not decreased or stopped when the patient sneezes). In yet other optional embodiments, the control portion 70 can be programmed to provide an alert (e.g., via the external device 68) upon determining or sensing a situation where voiding should happen (e.g., upon sensing that the bladder 10 is full). With these and related embodiments, a patient who might otherwise be un-aware of a need to void (for example due to poor health) is alerted of the circumstances (as is his or her caregiver in some embodiments). In yet other optional embodiments where the system includes or incorporates a motion-based transducer sensor (e.g., accelerometer sensor such as a three axes accelerometer as described above), the systems and methods of the present disclosure can include the control portion 70 being programmed to identify or recognize circumstances indicative of the patient desiring to void based upon posture and/or movement. For example, the control portion 70 can be programmed to identify certain movements by the patient in the middle of the night (e.g., the patient is determined to have arisen from a reclined position and/or is moving) as indicating the patient moving toward the bathroom and thus desires to void. Under these and similar circumstances, the control portion 70 can further be programmed to automatically reduce or suppress the delivery of stimulation energy otherwise being applied to activate the external urethral sphincter 34 and/or the external anal sphincter or other muscle for treating stress incontinence.

In other embodiments, the control portion 70 can be programmed to automatically suppress incontinence treatment stimulation energy upon determining that the patient's bladder 10 is full or nearly full (e.g., via any of the techniques described in the present disclosure) and determining a desire or need to void (e.g., based upon reference to one or more of EMG activity, relevant parasympathetic nerve activity, bioimpedance information, etc.). In related embodiments, the control portion 70 can be programmed to identify or recognize circumstances under which the patient is likely to be attempting to void and is experiencing difficulties in achieving a complete or nearly complete voiding of the bladder 10. For example, based upon one or more of the techniques described above, the control portion 70 can be programmed to recognize or identify an attempt to void or desired voiding event (e.g., that the patient's bladder 10 is full or nearly full, followed by a decrease in volume over a relatively short period of time); under these circumstances, the control portion 70 can be further programmed to monitor the desired voiding event, identifying a possible incomplete void (e.g., upon identifying the onset of a desired voiding event, the control portion 70 can monitor or estimate a volume of the bladder 10 as well as the change in volume over time; where the change in volume over time decreases below a predetermined threshold or absolute value (or some other comparison indicating that the patient's attempt at voiding is slowing down or nearing completion), the control portion 70 can be programmed to compare the current volume of the bladder 10 with a baseline or "empty" volume value. Where the determined current bladder volume exceeds the baseline or empty volume value by a predetermined amount or percentage, the control portion 70 can be programmed to recognize or designate that the patient is experiencing difficulties in achieving a complete or nearly complete void. Under these circumstances, the control portion 70 can be further programmed to automatically assist the patient in achieving a complete or nearly complete void. For example, the control portion 70 can be programmed to prompt the delivery of stimulation energy formatted to contract the detrusor muscle 30, prompt the delivery of stimulation energy formatted to increase parasympathetic drive, prompt the delivery of stimulation energy formatted to suppress relevant sympathetic nerve activity, etc.

In yet other embodiments, the systems and methods of the present disclosure optionally provide for stimulation therapy intended to facilitate desired voiding by the patient (e.g., in response to a patient prompt, based in whole or in part upon sensed information, etc.), for example by the control portion 70 being programmed to suppress or reduce delivery of stimulation energy intended to activate or contract the external urethral sphincter 34 as described above. Additionally or alternatively, the systems and methods of the present disclosure can include stimulating one or more of the hypogastric nerves at the T or L level or other nerve of the sympathetic nervous system relevant to bladder control and/or anal control (e.g., sympathetic nerves from T11, T12-L1, L2) in a manner that suppresses the relevant sympathetic nerve drive to thus encourage the natural micturition reflex (e.g., the body's natural, unconscious or reflexive control over voiding is suppressed). In optional related embodiments, the systems and methods of the present disclosure can include the control portion 70 being programmed, under circumstances where voiding is desired, to prompt the delivery of stimulation to target nerve(s) responsible for driving voiding such as the detrusor muscle, directly activing those muscle(s) while relaxing those intended to prevent accidental leakage. This optional approach may be beneficial for patients with incomplete control over the pelvic floor, such as patients who are convalescent, have spinal cord injury, are unconscious, etc.

External Device

As mentioned above, the systems of the present disclosure can optionally include one or more external devices 68. As a point of reference, the IMD 60 can be configured to interface (e.g., via telemetry) with a variety of external devices. For example, the external device 68 can include, but is not limited to, a patient remote, a physician remote, a clinician portal, a handheld device, a mobile phone, a smart phone, a desktop computer, a laptop computer, a tablet personal computer, etc. The external device 68 can include a smartphone or other type of handheld (or wearable) device that is retained and operated by the patient to whom the IMD 60 is implanted. In another example, the external device 68 can include a personal computer or the like that is operated by a medical caregiver for the patient. The external device 68 can include a computing device designed to remain at the home of the patient or at the office of the caregiver. Telemetry communication protocols are implemented in hardware and software, carried for example, by the IMD 60 and the external device 68. Standardized telemetry communication technology or protocol that can be used by one or more entities, in an open source or licensed arrangement. For example, Bluetooth®, Bluetooth® low energy (BLE), near-field magnetic induction (NFMI) communication, Wi-Fi, Zigbee®, etc.

In some embodiments, the external device 68 can be programmed (e.g., operate an installed software application) to provide a clinician with the ability to program various operational modes of the IMD 60. For example, where the external device 68 serves as a clinician programmer, the clinician can enter various performance attributes or protocols (e.g., stimulation levels, frequency, timing, etc.) that are operated upon by the IMD 60 (e.g., via the control portion 70).

In some embodiments, the external device 68 can be programmed (e.g., operate an installed software application) to provide a patient with the ability to control or adjust operation of the IMD 60. For example, where the external device 68 serves as a patient remote, the patient can be afforded the ability to adjust stimulation parameters in an effort to balance patient comfort with treatment efficacy. In addition or alternatively, the external device 68 can provide the patient with the ability to switch between pre-set groups of therapy parameters (e.g., the control portion 70 can be programmed to deliver stimulation energy at a first level in a first mode of operation and at a second level in a second mode of operation; the external device 68 can afford the patient the ability to select between the first and second modes of operation). With these and related embodiments, the external device 68 can provide the patient with the ability to stop the delivery of stimulation energy (or switch between modes of operation) to better ensure that the patient can void when desired and that the dynamic leak suppression therapy (for example) does not interfere with desired, normal voiding.

In one non-limiting example where the external device 68 is configured to serve as a patient remote, the patient can enter information at the external device indicating that an incontinence-related event, for example leakage, has just or very recently occurred. This event information is signaled to the control portion 70 that in turn is programmed to act upon the event information. For example, the control portion 70 can be programmed such that when otherwise operating to prompt delivery of stimulation energy intended to treat incontinence and a signal is received from the patient that a leakage event (or other incontinence event) has just or very recently occurred, the control portion 70 alters or increases the stimulation energy being delivered (e.g., increased amplitude, increased speed of response, increased duration of stimulation, etc.) in an effort to better address the patient's current needs. With these and related embodiments, the control portion 70 can effectively be programmed to prompt the delivery of less than "full strength" stimulation for treating incontinence in a normal mode of operation, and then increase or deliver "full strength" stimulation only when being informed by the patient of a need for such stimulation.

In yet other non-limiting embodiments, the systems and methods of the present disclosure can provide cloud based patient management (e.g., the external device 68 interfaces with the IMD 60 via the internet, Wi-Fi, etc.). With these and related embodiments, the systems and methods of the present disclosure can facilitate remote review or monitoring by a clinician of the therapy behavior being provided to the patient (e.g., dynamic event trigger) and/or the outcome of delivery therapy. Additionally or alternatively, the systems and methods of the present disclosure can facilitate a clinician remotely providing additional therapy instructions/protocols/modes of operation to the IMD 60, delete an existing programmed therapy delivery mode of operation, and/or modify parameters of an existing programmed therapy delivery mode of operation.

In yet other non-limiting embodiments of the present disclosure, the external device 68 can be programmed (e.g., operate an installed software application) that provides the patient with the ability to document information of interest, such as voiding and/or leaking events. The so-recorded information can be utilized by a clinician to assess therapy outcomes. In this regard, the clinician can review recorded information directly on the external device 68, or the recorded information can be delivered to a separate device (e.g., via the cloud) for clinician review. Where, for example, leakage events are reported by the patient on a patient remote, the so-reported information can be captured in a log such that an estimate of stimulation therapy effectiveness can be made.

In some example systems and methods of the present disclosure, stimulation parameters associated with one or more modes of operation provided by the control portion 70 can be generated as part of a trial or trialing protocol. For example, the systems and methods of the present disclosure can optionally include delivering the stimulation element 66 at a target location, and connecting the stimulation element 66 to an external stimulator (e.g., a pulse generator located external the patient). With this approach, the system can be operated to evaluate therapy response prior to full implant of the IPG 64. The stimulation element 66 can optionally be delivered trans-urethrally, or can be a chronic lead with a percutaneous adapter. In related embodiments, the trialing protocol can further include the sensor(s) 62 being implanted at the target location, or can be located external the patient at a position generating information representative of the future implanted sensor. For example, the sensor 62 utilized for the trialing protocol can be the actual sensor to be implanted in the future that is modified and attached to the patient's body with an adhesive, the trialing protocol can include use of an external-based impedance sensor system, etc.

In some embodiments, the control portion 70 is configured to provide the patient with the ability to temporarily de-activate the IMD 60 from delivering stimulation signals, for example via the external device 68.

UUI

Some example systems and methods of the present disclosure incorporate features (e.g., system components, programming, etc.) for treating UUI, for example by providing electrical stimulation to a targeted nerve, muscle, or other tissue at levels appropriate for reducing the sensation of a need or urge to empty the bladder 10 at times when the bladder 10 is not actually full or nearly full. With these and related embodiments, the systems and methods can include estimating or measuring or determining a current volume of the bladder 10 (e.g., information indicative of a current volume of the bladder 10 can be obtained by the sensor 62, and compared against predetermined bladder volume levels obtained, for example, by urodynamic assessment), along with patient-provided feedback of a perceived bladder volume or "urge" to void. Under circumstances where the estimated current volume of the bladder 10 is less than full yet the patient perceives a strong urge to void, the control portion 70 can be programmed to prompt the provision of appropriate stimulation energy to the targeted nerve and/or muscle sufficient to reduce the sensation of a need or urge to void. The control portion 70 can be further programmed to modulate delivered stimulation (e.g., increase intensity, delivery time, etc.) over time as the current volume of the bladder 10 increases (e.g., as determined, for example, from information provided by the sensor 62).

In related embodiments, the UUI treatment systems and methods of the present disclosure can include obtaining EMG information relative to the detrusor muscle 30 as described above. Current detrusor EMG information can, in turn, be correlated or useful to estimate current bladder volume, for example with reference to urodynamic assessment information of the patient. Under circumstances where the current detrusor EMG information indicates that the bladder 10 is less than full yet the patient is perceiving an urge to void (e.g., patient-provided feedback), the control portion 70 can be programmed to prompt the provision of appropriate stimulation energy to the targeted nerve and/or muscle sufficient to reduce the sensation of a need or urge to void. The control portion 70 can be further programmed to modulate delivered stimulation (e.g., increase intensity, delivery time, etc.) over time as the detrusor EMG information (and thus estimated bladder volume) increases. Alternatively or in addition, EMG information relative to the pelvic floor muscles 18 can be obtained and used as the basis for UUI stimulation treatment. For example, pelvic floor EMG information can be correlated with bladder volume. Under circumstances where the current pelvic floor EMG information indicates that the bladder 10 is less than full, yet the patient is perceiving an urge to void (e.g., patient-provided feedback), the control portion 70 can be programmed to prompt the provision of appropriate stimulation energy to the targeted nerve and/or muscle sufficient to reduce the sensation of a need or urge to void. The control portion 70 can be further programmed to modulate delivered stimulation (e.g., increase intensity, delivery time, etc.) over time as the pelvic floor EMG information (and thus estimated bladder volume) increases.

In related embodiments, the UUI treatment systems and methods of the present disclosure can include obtaining bioimpedance information indicative of a position of the pelvic floor muscles 18. The pelvic floor bioimpedance information can be correlated with bladder volume (e.g., via urodynamic assessment), and used as the basis for UUI stimulation therapy as described above.

The UUI treatment systems and methods of the present disclosure can optionally include sensing or detecting parasympathetic nerve activity otherwise indicative of an urge or desire to void the bladder 10 (e.g., via eletroneurography (ENG) techniques), for example by an electrode or other sensor component along one or more of the hypogastric nerves or the pelvic splanchnic nerves at the T or L level. With these and related embodiments, the control portion 70 can be programmed to detect or recognize parasympathetic nerve activity relevant to the bladder 10 and, under circumstances where relevant parasympathetic nerve activity is detected yet the bladder 10 is determined or estimated to be less than full, prompt the delivery of stimulation energy appropriate to suppress the parasympathetic nerve activity.

In some examples, the UUI treatment systems and methods of the present disclosure can include providing the patient with the external device 68 as described above, configured to provide the patient with the ability to select from two (or more) modes of operation. For example, the external device 68 can be configured to allow the patient to select or switch between an auto control mode and a continuous/open loop mode, with the selected mode of operation being signaled to the control portion 70 that in turn is programmed to prompt a provision of a corresponding UUI stimulation therapy or protocol. In the auto control mode, sensor feedback (e.g., as described above) is employed to determine whether or not stimulation energy is delivered and, where UUI stimulation energy is to be delivered, the format (e.g., level, timing, etc.) of such stimulation. In the continuous/open loop mode, UUI stimulation energy is delivered without reference to feedback information.

The UUI treatment systems and methods of the present disclosure can optionally include providing additional feedback to the patient via the external device 68, for example feedback information indicating a determination that the patient bladder 10 is full or nearly full (e.g., the control portion 70 is programmed to estimate bladder volume via one or more of the sensor-based parameters as described above such as detrusor EMG, pelvic floor EMG, bioimpedance, etc.). The patient, in turn, can understand from this feedback information a need to void his/her bladder and take appropriate action. In related embodiments, the external device 68 can be configured to provide the patient with an ability to better or more easily void his/her bladder when desired (e.g., after reviewing feedback information indicating that his/her bladder is full or nearly full, the patient can locate a bathroom or other locale where voiding is appropriate, and then operate the external device as described below). For example, the external device 68 can provide a button, switch, or the like, the actuation of which causes the control portion 70 to prompt the delivery of stimulation energy appropriate for activating or increasing a parasympathetic drive to void the bladder 10. Alternatively or in addition, the external device 68 can be configured such that the patient can cause the control portion 70 to prompt the reduction or suppression of incontinence stimulation energy (e.g., with optional embodiments in which the system is configured to provide incontinence stimulation therapy, for example delivering stimulation energy formatted to cause the external urethral sphincter 34 to activate or contract (for example by delivering stimulation energy to the pudendal nerve 44), the delivery of this incontinence stimulation energy can be reduced or suppressed when the patient is ready to void). In other, related embodiments, the systems and methods of the present disclosure can include informing the patient at the external device 68 of a need to void his/her bladder. The external device 68 can further request or otherwise facilitate the patient entering information indicating that he/she is currently ready to void; the control portion 70 can be programmed to automatically take action(s) that promote voiding (e.g., delivering stimulation energy formatted to contract the detrusor muscle 30, delivering stimulation energy formatted to increase parasympathetic drive, suppressing stimulation energy formatted to treat incontinence (e.g., suppressing stimulation energy otherwise formatted to cause the external urethral sphincter 34 to contract, etc.)).

The UUI treatment systems and methods of the present disclosure can further implements artificial intelligence or machine learning features. For example, through artificial intelligence or machine learning techniques, the control portion 70 can develop a customized therapy and/or sensing and diagnostics for the particular patient. With these and related embodiments, therapy titration could be simplified and could minimize or even eliminate the need for training with the help of urodynamic assessment.

In some examples a method comprises delivering, via the stimulation element 66 and during a treatment period, stimulation to a targeted nerve and/or muscle to treat incontinence and/or UUI. In some examples, the treatment period may comprise a period of time beginning with the patient turning on the therapy device and ending with the patient turning off the device. In some examples, the treatment period may comprise a selectable, predetermined start time (e.g. 6 a.m.) and selectable, predetermined stop time (e.g. 10 p.m.).

In some examples, the stimulation is applied during some of the treatment period without being delivered throughout the treatment period. Stated differently, in some examples stimulation may be performed during some portions of the treatment period but not during other portions of the same treatment period. In some examples, stimulation applied during the treatment period may comprise stimulation delivered throughout the treatment period. In some such examples, stimulation delivered throughout the treatment period may comprise stimulation being delivered throughout the entire treatment period. In some such examples, the term "throughout the entire" may comprise stimulation being performed in 100 percent of the treatment period. However, it will be understood that in some examples some startup routines, shutdown routines are not considered part of the 100 percent.

In some examples, stimulation being delivered throughout the treatment period comprises stimulation delivered throughout substantially the entire treatment period. In some such examples, in this context, the term "substantially the entire" comprises at least 70 percent, at least 80 percent, at least 90 percent, or at least 95 percent of the entire treatment period.

In some such examples, stimulation of the targeted nerve and/or muscle which is maintained during the treatment period may be referred to as being "on-going" in the treatment period but not continuous. For instance, the on-going stimulation may be implemented via a duty cycle, train of pulses, etc. such that the stimulation need not be one hundred percent continuous. Rather, in some such examples, the term "on-going" stimulation may refer to stimulation which does not start and/or stop based on occurrence of some event such as a controller signal to start stimulation or a controller signal to stop stimulation.

In some examples, stimulation of the targeted nerve and/or muscle may be performed via open loop stimulation. In some examples, the open loop stimulation may refer to performing stimulation without use of any sensory feedback of any kind relative to the stimulation.

Conversely, in some examples, stimulation of the targeted nerve and/or muscle may be performed via closed loop stimulation. In some examples, the closed loop stimulation may refer to performing stimulation at least partially based on sensory feedback regarding parameters of the stimulation and/or effects of the stimulation as described above.

Some of the systems and methods of the present disclosure have been described primarily as treating urinary incontinence in that they mitigate a stress urinary incontinence leak through functional stimulation in response to a pressure increase event. In other embodiments, the systems and methods of the present disclosure can optionally provide for or additionally include providing a therapeutic benefit through training of relevant muscles. For example, a training protocol or therapeutic mode can be programmed/implemented whereby stimulation is delivered on a schedule for creating muscle contraction of the sphincter and/or other continence muscles as a form of training, thereby providing a therapeutic effect of increasing continence muscle effectiveness. In some embodiments, the system is configured and programmed to operate in a treatment mode, a therapeutic mode, or both.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. For example, the systems and methods of the present disclosure can be utilized to treat other maladies, such as interstitial cystitis (IC). With IC treatment applications, one or more of the target sites discussed above are implicated. The delivered stimulation energy for treatment of IC can differ from that applied for the treatment of incontinence for example; in some embodiments, a larger and/or higher frequency stimulation energy as compared to that appropriate for treatment of incontinence.

The invention claimed is:

1. A method of treating incontinence of a patient, the method comprising:
    applying stimulation energy to a target site of the patient sufficient to activate an external sphincter of the patient;
    wherein the step of applying stimulation energy includes applying stimulation in a dynamic mode of operation comprising:
        determining onset of potential leakage, including:
            monitoring information from at least one sensor applied to the patient, the monitored information indicative of a physiological parameter of the patient,
            determining an instantaneous change in the monitored physiological parameter over time (dp/dt),
            determining that the instantaneous change in the monitored physiological parameter over time (dp/dt) meets a criteria; and
        automatically delivering stimulation energy in response to the determination that the instantaneous change in the monitored physiological parameter over time (dp/dt) meets the criteria.

2. The method of claim 1, wherein the step of applying stimulation energy further includes applying a low level stimulation energy and dynamically applying an additive stimulation energy to the low level stimulation energy.

3. The method of claim 1, wherein the step of applying stimulation energy further includes applying stimulation in a basal mode of operation comprising:
    delivering stimulation energy during time periods apart from time periods in which stimulation energy is being delivered in the dynamic mode of operation.

4. The method of claim 1, wherein the step of applying stimulation energy further includes applying stimulation in a basal mode of operation comprising modulating the applied stimulation energy to limit muscle stress or fatigue.

5. The method of claim 4, wherein the step of modulating includes at least one of:
    performing on/off duty cycles; and
    ramping the applied stimulation energy up and down.

6. The method of claim 4, wherein the target site is a first target site, and wherein the step of applying further comprises applying stimulation energy to a second target site, and further wherein the step of modulating includes applying stimulation energy to the first and second target sites on an alternating basis.

7. The method of claim 4, wherein the basal mode of operation further includes altering a level of applied stimulation in response to a sensed parameter of the patient.

8. The method of claim 7, wherein the sensed parameter is derived from a target site selected from the group consisting of a bladder of the patient, a urethra of the patient, a pelvic floor of the patient, an abdominal wall of the patient, and a rectum of the patient.

9. The method of claim 7, wherein the step of altering includes increasing a level of applied stimulation in response to an increase in the sensed parameter.

10. The method of claim 1, wherein the step of applying stimulation energy further includes applying stimulation in an urge mode of operation comprising:
    applying stimulation energy to a detrusor-related target site selected to prompt a detrusor muscle of the patient to relax.

11. The method of claim 10, wherein the detrusor-related target site is a pelvic floor nerve.

12. The method of claim 1, wherein the sensor is an accelerometer.

13. The method of claim 1, wherein the sensor is located to sense bioimpedance information of the patient.

14. The method of claim 1, wherein the sensor is located to sense EMG information of an anatomical feature of the patient selected from the group consisting of a detrusor muscle of the patient, an external urethral sphincter of the patient, an abdominal wall of the patient, a pelvic floor muscle of the patient, and an external anal sphincter of the patient.

15. The method of claim 1, wherein the step of determining that the instantaneous change in the monitored physiological parameter over time (dp/dt) meets a criteria includes determining that the instantaneous change in the monitored physiological parameter over time (dp/dt) meets the criteria over a predetermined number of sensing cycles such the step of automatically delivering stimulation energy in response to the determination does not occur unless the instantaneous change in the monitored physical parameter over time (dp/dt) is determined to have met the criteria for each cycle of the predetermined number of sensing cycles.

16. The method of claim 1, wherein the monitored physiological parameter is not a body position of the patient, and further wherein a value of the criteria is automatically selected as a function of a sensed body position of the patient.

17. The method of claim 1, wherein a level of stimulation delivered in response to the determination is automatically selected as a function of a sensed activity level of the patient.

18. The method of claim 1, wherein the step of automatically delivering stimulation energy includes selecting a level of the delivered stimulation energy as a function of the instantaneous change in the monitored physiological parameter over time (dp/dt).

19. The method of claim 1, wherein the step of automatically delivering stimulation energy includes selecting a level of the delivered stimulation energy as a function of a sensed activity level of the patient.

20. The method of claim 1, further comprising:
locating a first electrode at a first site of the patient, and locating a second electrode at a second site of the patient; and
operating the first and second electrodes to perform at least one of:
deliver stimulation to the first site and sense a parameter of the patient at the second site, and
sense a parameter of the patient at the first site and deliver stimulation to the second site.

21. The method of claim 1, wherein the step of automatically delivering stimulation energy further includes:
delivering stimulation energy at a first level when the instantaneous change in the monitored physiological parameter over time (dp/dt) meets a first criteria and the monitored parameter does not meet a second criteria; and
delivering stimulation energy at a second level greater than the first level when the instantaneous change in the monitored physiological parameter over time (dp/dt) meets the first criteria and the monitored parameter meets the second criteria.

22. The method of claim 1, wherein the monitored physiological parameter is indicative of one of bladder pressure, bladder fill volume, and abdominal pressure, the method further comprising:
monitoring a physical activity level of the patient;
delivering stimulation energy at a first level when the instantaneous change in the monitored physiological parameter over time (dp/dt) meets the criteria and the monitored physical activity level is below a threshold; and
delivering stimulation energy at a second level greater than the first level when the instantaneous change in the monitored physiological parameter over time (dp/dt) meets the criteria and the monitored physical activity level exceeds the threshold.

* * * * *